US010016486B1

(12) United States Patent
Pyun et al.

(10) Patent No.: US 10,016,486 B1
(45) Date of Patent: Jul. 10, 2018

(54) METHODS AND COMPOSITIONS USING AMPK ACTIVATORS FOR PHARMACOLOGICAL PREVENTION OF CHRONIC PAIN

(71) Applicant: ARIZONA BOARD OF REGENTS ON BEHALF OF THE UNIVERSITY OF ARIZONA, Tucson, AZ (US)

(72) Inventors: Dong-Chul Pyun, Tucson, AZ (US); Theodore J. Price, Tucson, AZ (US); Gregory D. Dussor, Tucson, AZ (US); Dipti Tillu, Tucson, AZ (US); Bo Lian, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 14 days.

(21) Appl. No.: 14/956,042

(22) Filed: Dec. 1, 2015

Related U.S. Application Data

(63) Continuation-in-part of application No. 14/318,245, filed on Jun. 27, 2014, now Pat. No. 9,233,085.

(60) Provisional application No. 61/840,886, filed on Jun. 28, 2013.

(51) Int. Cl.
| | |
|---|---|
| *A61K 31/05* | (2006.01) |
| *A61K 31/155* | (2006.01) |
| *A61K 31/4365* | (2006.01) |
| *A61K 31/7056* | (2006.01) |
| *A61K 31/4375* | (2006.01) |
| *A61K 31/4439* | (2006.01) |
| *A61K 31/616* | (2006.01) |
| *A61K 38/22* | (2006.01) |
| *A61K 38/02* | (2006.01) |
| *A61K 38/20* | (2006.01) |
| *A61K 38/18* | (2006.01) |

(52) U.S. Cl.
CPC .......... *A61K 38/2264* (2013.01); *A61K 31/05* (2013.01); *A61K 31/155* (2013.01); *A61K 31/4365* (2013.01); *A61K 31/4375* (2013.01); *A61K 31/4439* (2013.01); *A61K 31/616* (2013.01); *A61K 31/7056* (2013.01); *A61K 38/02* (2013.01); *A61K 38/185* (2013.01); *A61K 38/204* (2013.01)

(58) Field of Classification Search
CPC ............................. A61K 31/155; A61K 31/05
USPC .................. 514/635, 557, 733, 734
See application file for complete search history.

(56) References Cited

U.S. PATENT DOCUMENTS

2014/0186306 A1* 7/2014 Plante .................. A61K 31/155
424/93.7

OTHER PUBLICATIONS

Hasegawa-Moriyama et al. Peroxisome proliferator-activated receptor-gamma agonist rosiglitazone attenuates postincisional pain by regulating macrophase polarization. Biochemical and Biophysical Reasearch Communications 426 (2012) pp. 76-82.*

Asiedu, M.N., Tillu, D.V., Melemedjian, O.K., Shy, A., Sanoja, R., Bodell, B., Ghosh, S., Porreca, F., and Price, T.J. (2011). Spinal protein kinase M zeta underlies the maintenance mechanism of persistent nociceptive sensitization. The Journal of neuroscience : the official journal of the Society for Neuroscience 31, 6646-6653.

Banik, R.K., Subieta, A.R., Wu, C., and Brennan, T.J. (2005). Increased nerve growth factor after rat plantar incision contributes to guarding behavior and heat hyperalgesia. Pain 117, 68-76.

Banik, R.K., Woo, Y.C. Park, S. S., and Brennan, T.J. (2006). Strain and sex influence on pain sensitivity after plantar incision in the mouse. Anesthesiology 105, 1246-1253.

Boitano, S., Flynn, A.N., Schulz, S.M., Hoffman, J., Price, T.J., and Vagner, J. (2011). Potent agonists of the protease activated receptor 2 (PAR2). Journal of medicinal chemistry 54, 1308-1313.

Brennan, T.J., Vandermeulen, E.P., and Gebhart, G.F. (1996). Characterization of a rat model of incisional pain. Pain 64, 493-501.

Bryan, D., Walker, K.B., Ferguson, M., and Thorpe, R. (2005). Cytokine gene expression in a murine wound healing model. Cytokine 31, 429-438.

Chaplan, S.R., Bach, F.W., Pogrel, J.W., Chung, J.M., and Yaksh, T.L. (1994). Quantitative assessment of tactile allodynia in the rat paw. Journal of neuroscience methods 53, 55-63.

Crombie, I.K., Davies, H.T., and Macrae, W.A. (1998). Cut and thrust: antecedent surgery and trauma among patients attending a chronic pain clinic. Pain 76, 167-171.

(Continued)

*Primary Examiner* — Jennifer M Kim

(74) *Attorney, Agent, or Firm* — Nguyen & Tarbet Law Firm

(57) ABSTRACT

Methods and compositions using a combination of adenosine monophosphate protein kinase (AMPK) activators for treating pain such as post-surgical pain or development of chronic pain. The two or more AMPK activators work synergistically and may be administered in individually sub-efficacious doses. The AMPK activators may have different mechanisms of AMPK activation. The AMPK activators may be administered systemically and/or topically in, for example, as a gel, ointment, cream, lotion, suspension, liquid, or transdermal patch.

7 Claims, 11 Drawing Sheets
(10 of 11 Drawing Sheet(s) Filed in Color)

(56) References Cited

OTHER PUBLICATIONS

Flynn, A.N., Tillu, D.V., Asiedu, M.N., Hoffman, J., Vagner, J., Price, T.J., and Boitano, S. (2011). The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. The Journal of biological chemistry 286, 19076-19088.

Foretz, M., Hebrard, S., Leclerc, J., Zarrinpashneh, E., Soty, M., Mithieux, G., Sakamoto, K., Andreelli, F., and Viollet, B. (2010). Metformin inhibits hepatic gluconeogenesis in mice independently of the LKB1/AMPK pathway via a decrease in hepatic energy state. The Journal of clinical investigation 120, 2355-2369.

Fryer, L.G., Parbu-Patel, A., and Carling, D. (2002). The Antidiabetic drugs rosiglitazone and metformin stimulate AMP-activated protein kinase through distinct signaling pathways. The Journal of biological chemistry 277, 25226-25232.

Geranton, S.M., Jimenez-Diaz, L., Torsney, C., Tochiki, K.K., Stuart, S.A., Leith, J.L., Lumb, B.M., and Hunt, S.P. (2009). A rapamycin-sensitive signaling pathway is essential for the full expression of persistent pain states. The Journal of neuroscience : the official journal of the Society for Neuroscience 29, 15017-15027.

Goransson, O., McBride, A., Hawley, S.A., Ross, F.A., Shpiro, N., Foretz, M., Viollet, B., Hardie, D.G., and Sakamoto, K. (2007). Mechanism of action of A-769662, a valuable tool for activation of AMP-activated protein kinase. The Journal of biological chemistry 282, 32549-32560.

Huang, H.L., Cendan, C.M., Roza, C., Okuse, K., Cramer, R., Timms, J.F., and Wood, J.N. (2008). Proteomic profiling of neuromas reveals alterations in protein composition and local protein synthesis in hyper-excitable nerves. Molecular pain 4, 33.

Jimenez-Diaz, L., Geranton, S.M., Passmore, G.M., Leith, J.L., Fisher, A.S., Berliocchi, L., Sivasubramaniam, A.K., Sheasby, A., Lumb, B.M., and Hunt, S.P. (2008). Local translation in primary afferent fibers regulates nociception. PloS one 3, e1961.

Johansen, A., Romundstad, L., Nielsen, C.S., Schirmer, H., and Stubhaug, A. (2012). Persistent postsurgical pain in a general population: Prevalence and predictors in the Tromso study. Pain 153, 1390-1396.

Josan, J.S., Vagner, J., Handl, H.L., Sankaranarayanan, R., Gillies, R.J., and Hruby, V.J. (2008). Solid-Phase Synthesis of Heterobivalent Ligands Targeted to Melanocortin and Cholecystokinin Receptors. International journal of peptide research and therapeutics 14, 293-300.

Kehlet, H., Jensen, T.S., and Woolf, C.J. (2006). Persistent postsurgical pain: risk factors and prevention. Lancet 367, 1618-1625.

Lai, J.J., Lai, K.P., Chuang, K.H., Chang, P., Yu, I.C., Lin, W.J., and Chang, C. (2009). Monocyteimacrophage androgen receptor suppresses cutaneous wound healing in mice by enhancing local TNF-alpha expression. The Journal of Clinical Investigation 119, 3739-3751.

Lee, K.H., Hsu, E.G., Guh, J.H., Yang, H.C., Wang, D., Kulp, S.K., Shapiro, C.L., and Chen, C.S. (2011). Targeting energy metabolic and oncogenic signaling pathways in triple-negative breast cancer by a novel adenosine monophosphate-activated protein kinase (AMPK) activator. The Journal of biological chemistry 286, 39247-39258.

Matsuda, H., Koyama, H., Sato, H., Sawada, J., Itakura, A., Tanaka, A., Matsumoto, M., Konno, K., Ushio, H., and Matsuda, K. (1998). Role of nerve growth factor in cutaneous wound healing: accelerating effects in normal and healing-impaired diabetic mice. The Journal of experimental medicine 187, 297-306.

Melemedjian, O.K., Asiedu, M.N., Tillu, D.V., Peebles, K.A., Yan, J., Ertz, N., Dussor, G.O., and Price, T.J. (2010). IL-6- and NGF-induced rapid control of protein synthesis and nociceptive plasticity via convergent signaling to the eIF4F complex. The Journal of neuroscience : the official journal of the Society for Neuroscience 30, 15113-15123.

Ouyang, J., Parakhia, R.A., and Ochs, R.S. (2011). Metformin activates AMP kinase through inhibition of AMP deaminase. The Journal of biological chemistry 286, 1-11.

Pogatzki, E.M., and Raja, S.N. (2003). A mouse model of incisional pain. Anesthesiology 99, 1023-1027.

Sanders, M.J., Ali, Z.S., Hegarty, B.D., Heath, R., Snowden, M.A., and Carling, D. (2007). Defining the mechanism of activation of AMP-activated protein kinase by the small molecule A-769662, a member of the thienopyridone family. The Journal of biological chemistry 282, 32539-32548.

Sato, Y., and Ohshima, T. (2000). The expression of mRNA of proinflammatory cytokines during skin wound healing in mice: a preliminary study for forensic wound age estimation (II). International journal of legal medicine 113, 140-145.

Shaw, R.J., Lamia, K.A., Vasquez, D., Koo, S.H., Bardeesy, N., Depinho, R.A., Montminy, M., and Cantley, L.C. (2005). The kinase LKB1 mediates glucose homeostasis in liver and therapeutic effects of metformin. Science 310, 1642-1646.

Vagner, J., Xu, L., Handl, H.L., Josan, J.S., Morse, D.L., Mash, E.A., Gillies, R.J., and Hruby, V.J. (2008). Heterobivalent ligands crosslink multiple cell-surface receptors: the human melanocortin-4 and delta-opioid receptors. Angewandte Chemie 47, 1685-1688.

Notice of Allowance issued in U.S. Appl. No. 14/318,245, dated Aug. 18, 2015.

* cited by examiner

US 10,016,486 B1

METHODS AND COMPOSITIONS USING AMPK ACTIVATORS FOR PHARMACOLOGICAL PREVENTION OF CHRONIC PAIN

CROSS REFERENCE

This application is a continuation-in-part of U.S. patent application Ser. No. 14/318,245 filed Jun. 27, 2014 which claims priority to and is a non-provisional of U.S. Provisional Patent Application No. 61/840,886, filed Jun. 28, 2013, the specification(s) of which is/are incorporated herein in their entirety by reference.

GOVERNMENT SUPPORT

This invention was made with government support under grant number R01 GM102575 awarded by the National Institutes of Health (NIH). The government has certain rights in the invention.

FIELD OF THE INVENTION

The present invention relates to methods and compositions for treating pain, more particularly to methods and compositions featuring two (or more) different 5' adenosine monophosphate-activated protein kinase (AMPK) activators for treating pain, for example post-surgical pain (e.g., pain at an incision site, etc.).

BACKGROUND OF THE INVENTION

Chronic pain following surgical incisions is a major clinical problem. As used herein, the term "chronic pain" refers to pain lasting at least three (3) months and typically at least six (6) months, e.g., after surgery, injury or a disease. Currently available therapeutics given for acute post-surgical pain (e.g., opiates and non-steroidal anti-inflammatory drugs, i.e., NSAIDs) do not always prevent the transition to chronic post-surgical pain. Furthermore, opiates and NSAIDs can be habit forming and/or patients develop tolerance to these drugs, thereby requiring increased dosage. Moreover, because these drugs are typically administered orally, many patients suffer adverse gastrointestinal discomfort.

The present invention features AMPK activation as a mechanism for the alleviation of post-surgical, and possibly other persistent pain states and utilization of novel therapeutics that employ this mechanism of action of use in humans. Dysregulated protein translation regulation pathways that underlie persistent pain states can be negatively regulated by activation of endogenous signaling factor AMPK.

As such, the present invention features methods and compositions that use AMPK activators for treating pain, e.g., acute post-surgical pain, transition to chronic pain, etc. (pain may be measured using various parameters including but not limited to acute hypersensitivity and hyperalgesic priming, etc.). The methods and compositions of the present invention may feature a first AMPK activator and a second AMPK activator, wherein the two AMPK activators work synergistically and the AMPK activators are administered in individually sub-efficacious doses. In some embodiments, AMPK activators that have different mechanisms of AMPK activation, such as metformin and resveratrol, are used to accomplish this.

SUMMARY OF INVENTION

The present invention features methods for treating, reducing, or preventing the development of pain (e.g., post-surgical pain, e.g., incision-induced hypersensitivity, incision-induced hyperalgesic priming, incision-induced development of chronic pain, etc.). In some embodiments, the method comprises administering to a subject a dosage of a first 5'-adenosine monophosphate-activated protein kinase (AMPK) activator and a dosage of a second AMPK activator, wherein the second AMPK activator has a mechanism of AMPK activation that is different from that of the first AMPK activator. The dosage of the first AMPK activator may be an individually sub-efficacious dose, and the dosage of the second AMPK activator may be an individually sub-efficacious dose, wherein the first AMPK activator and the second AMPK activator synergistically reduce, treat, or prevent the development of said pain, e.g., post-surgical pain, e.g., incision-induced hypersensitivity, incision-induced hyperalgesic priming, incision-induced development of chronic pain, etc.

The present invention also features compositions for treating, reducing, or preventing the development of pain (e.g., post-surgical pain, e.g., incision-induced hypersensitivity, incision-induced hyperalgesic priming, incision-induced development of chronic pain, etc.). In some embodiments, the composition comprises a dosage of a first 5'-adenosine monophosphate-activated protein kinase (AMPK) activator and a dosage of a second AMPK activator, wherein the second AMPK activator has a mechanism of AMPK activation that is different from that of the first AMPK activator. The dosage of the first AMPK activator may be an individually sub-efficacious dose, and the dosage of the second AMPK activator may be an individually sub-efficacious dose, wherein the first AMPK activator and the second AMPK activator function synergistically reduce, treat, or prevent the development of said pain, e.g., post-surgical pain, e.g., incision-induced hypersensitivity, incision-induced hyperalgesic priming, incision-induced development of chronic pain, etc.

In some embodiments, the sub-efficacious dose of the first AMPK activator is a dose that is less than the first AMPK activator's threshold dose. In some embodiments, the sub-efficacious dose of the first AMPK activator is a dose that is less than the first AMPK activator's $EC_{50}$. In some embodiments, the sub-efficacious dose of the first AMPK activator is a dose that is between the first AMPK activator's $EC_{50}$ and threshold dose.

In some embodiments, the sub-efficacious dose of the second AMPK activator is a dose that is less than the second AMPK activator's threshold dose. In some embodiments, the sub-efficacious dose of the second AMPK activator is a dose that is less than the second AMPK activator's $EC_{50}$. In some embodiments, the sub-efficacious dose of the second AMPK activator is a dose that is between the second AMPK activator's $EC_{50}$ and threshold dose.

In some embodiments, the first AMPK activator comprises a biguanide and the second AMPK activator comprises a natural compound. In some embodiments, the first AMPK activator comprises a biguanide and the second AMPK activator comprises a thiazolidinedione. In some embodiments, the first AMPK activator comprises a thiazolidinedione and the second AMPK activator comprises a natural compound. In some embodiments, the first AMPK activator comprises a biguanide and the second AMPK activator comprises a hormone. In some embodiments, the first AMPK activator comprises a hormone and the second AMPK activator comprises a natural compound. The method of claim 1, wherein the first AMPK activator comprises a thiazolidinedione and the second AMPK activator comprises a hormone.

In some embodiments, the first AMPK activator comprises a biguanide and the second AMPK activator comprises a molecule selected from the group consisting of A769662, salicylate or a derivative thereof, AICAR, PT1, C24, and OSU53. In some embodiments, the first AMPK activator comprises a natural compound and the second AMPK activator comprises a molecule selected from the group consisting of A769662, salicylate or a derivative thereof, AICAR, PT1, C24, and OSU53. In some embodiments, the first AMPK activator comprises a hormone and the second AMPK activator comprises a molecule selected from the group consisting of A769662, salicylate or a derivative thereof, AICAR, PT1, C24, and OSU53. In some embodiments, the first AMPK activator comprises a thiazolidinedione and the second AMPK activator comprises a molecule selected from the group consisting of A769662, salicylate or a derivative thereof, AICAR, PT1, C24, and OSU53.

In some embodiments, the biguanide is selected from the group consisting of metformin, phenformin, buformin, and proguanil. In some embodiments, the natural compound is selected from the group consisting of resveratrol, berberine, galegine, quercetin, ginsenoside, curcumin, epigallocatechin gallate, theaflavin, hispidulin, rooibos, and alpha-lipoic acid. In some embodiments, the thiazolidinedione is selected from the group consisting of pioglitazone and rosiglitazone. In some embodiments, the hormone is selected from the group consisting of adiponectin, leptin, IL-6, and ciliary neurotrophic factor (CNTF).

In some embodiments, the dosage of the first AMPK activator is a local dosage or a systemic dosage. In some embodiments, the dosage of the second AMPK activator is a local dosage or a systemic dosage. In some embodiments, the dosages of the first AMPK activator and the second AMPK activator are administered at a time that is between 24 hours before and 24 hours after a surgical incision is made.

BRIEF DESCRIPTION OF THE DRAWINGS

This patent application contains at least one drawing executed in color. Copies of this patent or patent application publication with color drawing(s) will be provided by the Office upon request and payment of the necessary fee.

DETAILED DESCRIPTION OF THE INVENTION

Surgery is a major cause of persistent pain suggesting that treatments that directly target the molecular pathology promoting post-surgical pain, particularly those that contribute to the progression to chronic pain, are needed. The present inventors have previously demonstrated that dysregulated protein translation regulation pathways, in particular ERK/eIF4E and mTOR signaling pathways underlie persistent pain states and that AMPK activators can profoundly inhibit ERK and mTOR signaling in sensory neurons. Furthermore, the present inventors have discovered that local injection of resveratrol, a potent AMPK activator, into the hindpaw following plantar incision dose-relatedly reverses incision-mediated mechanical hypersensitivity as well as hyperalgesic priming induced by incision.

Surprisingly and unexpectedly, the present inventors have further discovered that a topical application of an AMPK activator, such as resveratrol, resulted in a bona-fide mechanism for the alleviation of post-surgical, and other persistent or chronic pain states.

Thus, some aspects of the present invention provide a topical composition comprising an AMPK activator or a combination if AMPK activators and using said AMPK activators to treat pain, e.g., pain associated with post-surgery as well as other acute and neuropathy pain, including pain due to injury or disease. In addition, compositions and methods of the invention may be used to prevent any acute injury from developing into a chronic pain.

In some embodiments, the composition comprises one AMPK activator. In some embodiments, the composition comprises two AMPK activators. In some embodiments, the composition comprises three AMPK activators. In some embodiments, the composition comprises four AMPK activators. In some embodiments, the composition comprises more than four AMPK activators.

The AMPK activators in the composition may have different mechanisms of AMPK activation. In some embodiments, some of the AMPK activators in the composition may have similar mechanisms of AMPK activation. In some embodiments, some of the AMPK activators in the composition may have different mechanisms of AMPK action.

AMPK activators may include but are not limited to: biguanides (e.g., metformin, phenformin, buformin, proguanil, etc.); thiazolidinediones (TZDs) (e.g., pioglitazone, rosiglitazone, etc.), salicylates, hormones (e.g., adiponectin, leptin, IL-6, CNTF, etc.), natural compounds (e.g., resveratrol, polyphenols, berberine, galegine, quercetin, ginsenoside, curcumin, epigallocatechin gallate, theaflavin, hispidulin, rooibos, alpha-lipoic acid, etc.) and other molecules (e.g., PT1, C24, OSU53, A769662, AICAR, etc.).

Figure 10:
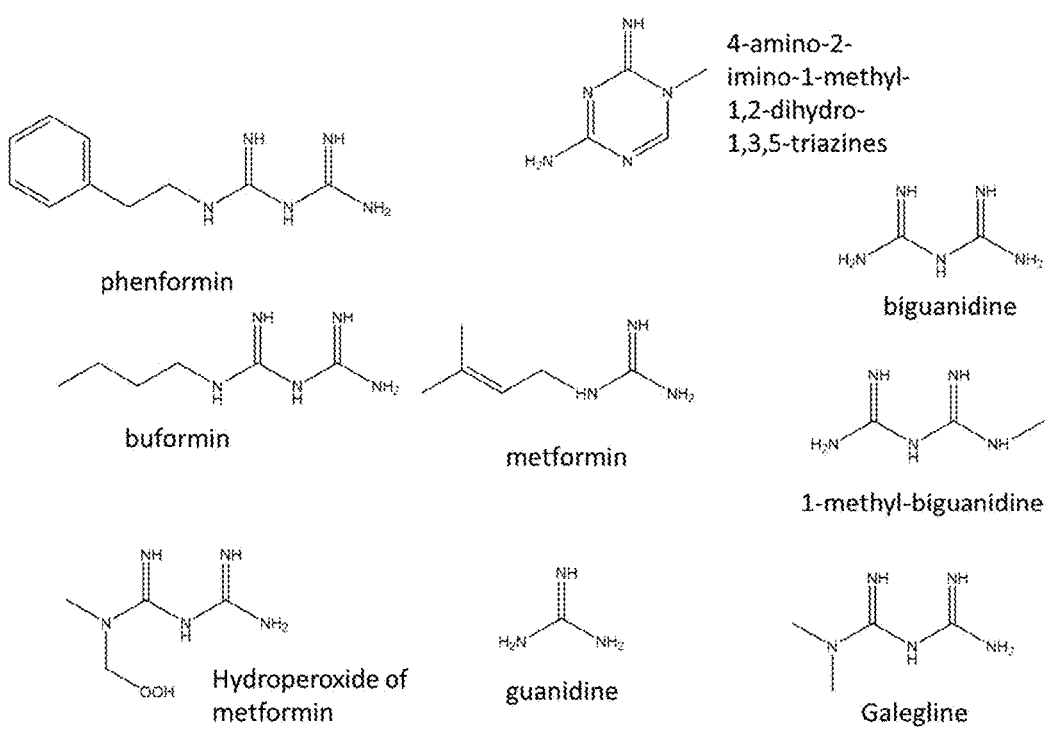
FIG. 10 shows examples of drugs/derivatives related to metformin including phenformin, buformin, biguanidine, 1-methyl-biguanidine, galegline, guanidine, hydroperoxide of metformin, and 4-amino-2-imino-1-methyl-1,2-dihydro-1,3,5-triazines.

FIG. 10 shows various examples of drugs/derivatives related to metformin including phenformin, buformin, biguanidine, 1-methyl-biguanidine, galegline, guanidine, hydroperoxide of metformin, and 4-amino-2-imino-1-methyl-1,2-dihydro-1,3,5-triazines. In some embodiments, the AMPK activator comprises phenformin, buformin, biguanidine, 1-methyl-biguanidine, galegline, guanidine, hydroperoxide of metformin, and 4-amino-2-imino-1-methyl-1,2-dihydro-1,3,5-triazines. In some embodiments, the AMPK activator comprises said drugs/derivatives related to metformin, their pharmaceutically acceptable salts, pharmaceutical compositions comprising said drugs/derivatives, etc. For example, in some embodiments, the AMPK activator comprises a prodrug wherein sulfur-containing promoieties are attached to metformin to form novel bioreversible sulfenyl guanidine (N-S) prodrugs of metformin. In some embodiments, said bioreversible sulfenyl guanidine (N-S) prodrugs of metformin have improved oral absorption as compared to metformin.

The present invention is not limited to the aforementioned AMPK activators (AMPK activators are well known to one skilled in the art, see, for example, Merck Index, 15$^{th}$ Ed., Edited by Maryadele J O'Neil, Royal Society of Chemistry, 2013, and Physicians' Desk Reference 67$^{th}$ Ed., 2013, all of which are incorporated herein by reference in their entirety).

In some embodiments, the sub-efficacious dose of the AMPK activator is a dose that is less than its threshold dose of the AMPK activator, the threshold dose being a dose that is the minimum dose of a drug needed to produce a measurable response. In some embodiments, the sub-efficacious dose of the AMPK activator is a dose that is less than the $EC_{50}$ of the AMPK activator. In some embodiments, the sub-efficacious dose of the AMPK activator is a dose that is between the $EC_{50}$ and the threshold dose of the AMPK activator.

In some embodiments, the sub-efficacious dose of the AMPK activator is less than a relative threshold dose, wherein a relative threshold dose is a minimum dose of a drug that is needed to produce a response that is equivalent to the threshold dose of metformin or resveratrol. For example, if a threshold dose of a compound is not known, a relative threshold dose may be determined by finding a dose that produces the same effect as the threshold dose of metformin or the threshold dose of resveratrol; that dose may be considered a relative threshold dose and used accordingly.

In some embodiments, the composition (or the method) uses a first AMPK activator and a second AMPK activator. In some embodiments, the first AMPK activator comprises a biguanide and the second AMPK activator comprises a natural compound. In some embodiments, the first AMPK activator comprises a biguanide and the second AMPK activator comprises a thiazolidinedione. In some embodiments, the first AMPK activator comprises a thiazolidinedione and the second AMPK activator comprises a natural compound. In some embodiments, the first AMPK activator comprises a biguanide and the second AMPK activator comprises a hormone. In some embodiments, the first AMPK activator comprises a hormone and the second AMPK activator comprises a natural compound. In some embodiments, the first AMPK activator comprises a thiazolidinedione and the second AMPK activator comprises a hormone. In some embodiments, the first AMPK activator comprises a biguanide and the second AMPK activator comprises a molecule selected from the group consisting of A69662, salicylate or a derivative thereof, AICAR, PT1, C24, and OSU53. In some embodiments, the first AMPK activator comprises a natural compound and the second AMPK activator comprises a molecule selected from the group consisting of A769662, salicylate or a derivative thereof, AICAR, PT1, C24, and OSU53. In some embodiments, the first AMPK activator comprises a hormone and the second AMPK activator comprises a molecule selected from the group consisting of A769662, salicylate or a derivative thereof, AICAR, PT1, C24, and OSU53. In some embodiments, the first AMPK activator comprises a thiazolidinedione and the second AMPK activator comprises a molecule selected from the group consisting of A769662, salicylate or a derivative thereof, AICAR, PT1, C24, and OSU53.

In some embodiments, the biguanide is selected from the group consisting of metformin, phenformin, buformin, and proguanil. In some embodiments, the natural compound is selected from the group consisting of resveratrol, berberine, galegine, quercetin, ginsenoside, curcumin, epigallocatechin gallate, theaflavin, hispidulin, rooibos, and alpha-lipoic acid. In some embodiments, the thiazolidinedione is selected from the group consisting of pioglitazone and rosiglitazone. In some embodiments, the hormone is selected from the group consisting of adiponectin, leptin, IL-6, and ciliary neurotrophic factor (CNTF).

In some embodiments, the dosage of the first AMPK activator is a local dosage or a systemic dosage. In some embodiments, the dosage of the second AMPK activator is a local dosage or a systemic dosage. In some embodiments, the dosages of the first AMPK activator and the second AMPK activator are administered at a time that is between 24 hours before and 24 hours after a surgical incision is made.

In some embodiments, the AMPK activators are administered topically, e.g., the composition is a topical composition. In some embodiments, the AMPK activators are administered systemically. In some embodiments, one of AMPK activators is administered topically and one AMPK activator is administered systemically. As previously discussed, the AMPK activators that are used in combination can possess different or similar mechanisms of AMPK activation.

The present invention also features a method for treating acute pain or preventing the development of chronic pain in a subject, said method comprising applying and/or administering a first AMPK activator and a second AMPK activator. In some embodiments, the method of administering said AMPK activators is selected from among: a. administering topically; b. administering systemically; or c. administering parenterally.

In some embodiments, the topical formulation further comprises a topical base, wherein the topical base is polyethylene glycol (PEG 400). In some embodiments, the topical formulation is in a form of a cream, a lotion, an ointment, a gel, a transdermal patch or a liquid solution.

In some embodiments, the pain comprises a post-surgical pain, neuropathic pain, or any pain potentially leading to the development of chronic post-surgical pain.

In some embodiments, a concentration of resveratrol in the topical formulation is between about 0.5 mg/ml and 5 mg/ml. In some embodiments, the concentration of resveratrol in the topical formulation is between about 1 mg/ml and 3 mg/ml. In some embodiments, the concentration of resveratrol in the topical formulation is between about 1.5 mg/ml and 2.5 mg/ml.

In some embodiments, a concentration of metformin in the topical formulation is between about 0.5 mg/ml and 5 mg/ml. In some embodiments, the concentration of metformin in the topical formulation is between about 1 mg/ml and 3 mg/ml. In some embodiments, the concentration of metformin in the topical formulation is between about 1.5 mg/ml and 2.5 mg/ml.

In some embodiments, the topical formulation is applied on and around an incision immediately following incision. In some embodiments, the topical formulation is applied on and around an incision immediately following incision and at about 24 hours following incision. In some embodiments, the topical formulation is applied on and around an incision between about 30 seconds and one minute following incision. In some embodiments, the topical formulation is applied on and around an incision between about one minute and five minutes following incision. In some embodiments, the topical formulation is applied on and around an incision between about five minutes and ten minutes following incision. In some embodiments, the topical formulation is applied on and around an incision between about ten minutes and thirty minutes following incision. In some embodiments, the topical formulation is applied on and around an incision between about thirty minutes and one hour following incision. In some embodiments, the topical formulation is applied on and around an incision about every three to four hours following incision. In some embodiments, the topical formulation is applied on and around an incision about 24 hours following incision. In some embodiments, the topical formulation is applied on and around an incision about 24 hours following incision.

In some embodiments, the topical formulation is applied to an incision site at about 24 hours prior to incision. In some embodiments, the topical formulation is applied to an incision site at about 48 hours prior to incision. In some embodiments, the topical formulation is applied to an incision site at about every four to six hours for about two days prior to incision. In some embodiments, the topical formulation is applied on and around an incision site at about every two to four days, starting at about two days prior to incision, and up to the fourteenth day following incision.

In some embodiments, the dosage of resveratrol is between about 1 mg/kg to about 5 mg/kg. In some embodiments, the dosage of resveratrol is between about 5 mg/kg to about 10 mg/kg. In some embodiments, the dosage of resveratrol is between about 10 mg/kg to about 15 mg/kg. In some embodiments, the dosage of resveratrol is between about 15 mg/kg to about 25 mg/kg. In some embodiments, the dosage of resveratrol is between about 25 mg/kg to about 35 mg/kg. In some embodiments, the dosage of resveratrol is between about 35 mg/kg to about 50 mg/kg. In some embodiments, the dosage of resveratrol is between about 35 mg/kg to about 50 mg/kg.

In some embodiments, the dosage of metformin is between about 1 mg/kg to about 5 mg/kg. In some embodiments, the dosage of metformin is between about 5 mg/kg to about 10 mg/kg. In some embodiments, the dosage of metformin is between about 10 mg/kg to about 20 mg/kg. In some embodiments, the dosage of metformin is between about 20 mg/kg to about 30 mg/kg. In some embodiments, the dosage of metformin is between about 30 mg/kg to about 50 mg/kg. In some embodiments, the dosage of metformin is between about 50 mg/kg to about 100 mg/kg. In some embodiments, the dosage of metformin is between about 100 mg/kg to about 150 mg/kg. In some embodiments, the dosage of metformin is between about 150 mg/kg to about 200 mg/kg. In some embodiments, the dosage of metformin is between about 200 mg/kg to about 250 mg/kg. In some embodiments, the dosage of metformin is between about 250 mg/kg to about 300 mg/kg.

In one particular embodiment, a topical composition comprising resveratrol is prepared as a cream. Briefly, lyophilized resveratrol was serially dissolved in polyethylene glycol 400 (PEG 400) and solid PEG ointment to achieve a final concentration of 2 mg/ml. Using the plantar incision model in mice, the present inventors demonstrated that topical application of resveratrol attenuated incision-induced mechanical hypersensitivity as well as the development of hyperalgesic priming precipitated by hind paw injection of $PG_{E2}$ following resolution of incision-induced mechanical hypersensitivity. Metformin, which is clinically available and widely prescribed, stimulated upstream LKB1 activity to activate AMPK whereas OSU-53 and A-769662 are positive allosteric modulators that directly activate AMPK.

Using the Brennan incision model in mice, the present inventors have demonstrated that systemic metformin or local OSU-53 injection dose-dependently and efficaciously attenuated incision-induced mechanical hypersensitivity as well as the development of hyperalgesic priming precipitated by hind paw injection of $PGE_2$ following resolution of incision-induced mechanical hypersensitivity. Interestingly, systemic A-769662 was not effective in blocking incision-induced acute mechanical hypersensitivity; however it significantly blocked hyperalgesic priming. This effect was paralleled by lower doses of metformin, which had no acute effect yet blocked hyperalgesic priming. Finally, co-treatment with systemic metformin and local resveratrol at individually sub-efficacious doses at the time of incision blocked acute hypersensitivity and hyperalgesic priming suggesting potential synergistic or super-additive effects of combined AMPK activator use. None of these treatment approaches adversely affected wound healing. These results provide further evidence for activation of AMPK as a novel treatment avenue for acute and chronic pain states induced by surgery.

Post-surgical pain has been identified as a potential major cause for chronic pain. Between 10 and 50% of patients who undergo surgery develop chronic pain following surgical procedures such as groin hernia repair, breast and thoracic surgery, leg amputation, or coronary artery bypass surgery (Kehlet et al., 2006) and up to a quarter of all chronic pain patients suffer from persistent pain because of a prior surgery (Crombie et al., 1998). This chronic pain can be debilitating in 2-10% of this population (Johansen et al., 2012; Kehlet et al., 2006). Despite the fact that analgesics for the treatment of acute post-surgical pain are widely available, surgery remains a major cause of persistent pain suggesting that treatments that directly target the molecular pathology of post-surgical pain, particularly those that prevent the transition to chronic post-surgical pain, are needed. Recent advances in understanding of the mechanisms of post-surgical pain have led to the elucidation of signaling pathways and mediators that play an important role in driving post-surgical pain. However, treatment approaches that target these pathways or mediators are not currently clinically utilized.

The present inventors have previously demonstrated that dysregulated protein translation regulation pathways, in particular ERK and mTOR signaling pathways, underlie persistent pain states such as neuropathic pain. There is an upregulation of the mTOR and ERK signaling pathways in neuropathic pain models in rodents and ectopic activity of the peripheral nerves (Geranton et al., 2009; Huang et al., 2008; Jimenez-Diaz et al., 2008). In model of post-surgical pain, there is an increase in IL-6 and NGF levels in the serum and skin around the incision (Banik et al., 2005; Bryan et al., 2005; Matsuda et al., 1998; Sato and Ohshima, 2000). IL-6 and NGF, in turn, signal through ERK and mTOR pathways inducing nociceptive sensitization (Melemedjian et al., 2010). The present inventors have recently demonstrated that both these pathways can be negatively regulated by an endogenous signaling factor, adenosine monophosphate protein kinase (AMPK). AMPK is a ubiquitous energy-sensing kinase which can be activated physiologically by increase in intracellular AMP/ATP ratio which occurs during energy deprivation or cell starvation. AMPK can be activated pharmacologically as well by a number of clinically available drugs, e.g., metformin or natural products such as resveratrol. AMPK can also be activated by a number of investigational compounds e.g. AICAR, A769662 or OSU53. The present inventors have demonstrated that the AMP activated protein kinase (AMPK) activators, metformin and A769662, inhibited translation regulation signaling pathways and nascent protein synthesis in injured nerves neurons resulting in a resolution of neuropathic allodynia induced by peripheral nerve injury. In addition, the present inventors also demonstrated that resveratrol, a potent and efficacious activator of AMPK, profoundly inhibits ERK and mTOR signaling in sensory neurons in a time- and concentration-dependent fashion and local injection of resveratrol around the surgery site attenuates the surgery induced acute mechanical hypersensitivity and persistent hyperalgesic priming in a model of post-surgical pain.

The present inventors have discovered that AMPK activation is a bona-fide mechanism for the alleviation of post-surgical, and other persistent pain states. Some aspects of the invention are based on this discovery to provide novel therapeutics and therapeutic strategies that employ this mechanism of action for use in mammals such as humans. As discussed in the Examples section, the present inventors have utilized multiple AMPK activators, including resveratrol, metformin, OSU-53 and A-769662, which possess different mechanisms of AMPK activation to demonstrate a shared endpoint—inhibition of incision-induced mechanical hypersensitivity and hyperalgesic priming.

The advantages of the topical route of drug administration include: avoidance of the risks and inconvenience of parenteral treatment; avoidance of the variable absorption and metabolism associated with oral treatment; continuity of drug administration, permitting use of pharmacologically active agents with short biological half-lives; potential reduction of gastrointestinal irritation in systemic administration; and treatment of cutaneous manifestations of diseases usually treated systemically.

In some embodiments, an AMPK activator is formulated for topical administration to the epidermis as a solution, gel, ointment, cream, suspension, lotions, a transdermal patch etc. as are well-known in the art. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

In some embodiments, the topical formulation is a liquid, for example, a homogeneous liquid or a suspension, sold in a bottle which dispenses the formulation as drops or a liquid film (for example, from an applicator tip that contacts a target area of the skin to dispense the liquid substantially only on a target area of the skin to be treated). In one embodiment, the formulation is a cream or ointment, sold in a tube which dispenses the formulation to a target area of the skin. In another embodiment, the AMPK activator is provided in a viscous liquid (such as carboxylmethylcellulose, hydroxypropyl-methylcellulose, polyethylene glycol, glycerin, polyvinyl alcohol, or oil containing drops) for rubbing into the skin. The formulations may have preservatives or be preservative-free (for example in a single-use container). One embodiment is any of the aforementioned formulations in a kit for topical or local administration.

Particular embodiments of the topical formulations include a therapeutically effective amount of the AMPK activator, a topical base, an antioxidant, an emollient, and an emulsifier. The topical base may comprise polyethylene glycol having a selected molecular weight. Particular embodiments comprise a polyethylene glycol having a molecular weight of from 3000 to 8000 daltons as a topical base. Topical bases include, but are not limited to, hydrophobic vehicles such as hydrocarbons, liquid petrolatum (mineral oil, liquid paraffin, paraffin oil), white petrolatum (petroleum jelly, VASELINE®), yellow petrolatum (petroleum jelly), squalane (perhydrosqualene, spinacane), and silicones; silicones such as liquid polydimethylsiloxanes (dimethicone, silastic, medical grade silicone oil), alcohols such as lauryl alcohols (1-dodecanol, dodecyl alcohols), myristyl alcohols, (tetradecanol, tetradecyl alcohols), cetyl alcohols (hexadecanol, ethal, palmityl alcohols), stearyl alcohols (stenol, cetosteryl alcohols), oleyl alcohols (ocenol); sterols such as sterol esters; lanolin such as hydrous wool fat, lanum; anhydrous lanolin (such as wool fat, anhydrous lanum, agnin); semi synthetic lanolins; carboxylic acids such as lauric acid, myristic acid, palmitic acid, stearic acid, oleic acid; esters and polyesters, such as cholesterol esters (stearate), ethylene glycol monoesters, propylene glycol monoesters, glyceryl monoesters, glyceryl monostearate, sorbitol monoesters, sorbitan monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, isopropyl palmitate; and ethers and polyethers (polydisperse or monodisperse), such as polyethylene glycols or polypropylene glycols (pluronics).

In certain embodiments, the formulation is an ointment, which is a semisolid preparation intended for external application to the skin or mucous membranes. In a specific example, the ointment is based on petrolatum. The ointment does not contain sufficient water to separate into a second phase at room temperature. A water-soluble ointment may be formulated with a water-miscible solvent. Ointments are ideal emollients with good skin penetration and adherence to surfaces. The ointment is in a convenient container such as a tube or jars.

In some embodiments, the water-miscible solvent is polyalkylene glycol having an average molecular weight of from 200 daltons to 600 daltons. In certain embodiments the water-miscible solvent comprises PEG-400, and even more particularly PEG-400 substantially free of impurities. In certain embodiments, the PEG-400 comprises less than 65 ppm formaldehyde, less than 10 ppm formaldehyde, or 1 ppm or less formaldehyde. In one aspect, the water-miscible solvent includes glycofurol, which can be used in place of or in combination with a low molecular weight polyalkylene glycol, particularly a polyethylene glycol, such as PEG-400. Water-miscible solvents that may be used, but are not limited to, include polyols and polyglycols such as propylene glycol (1,2-propanediol), glycerin (glycerol), liquid polyethylene glycol, solid polyethylene glycol (hard macrogol, carbowax®), glycol furol, 1,2- phenol-hexanetriol, sorbitol solution, esters and polyesters such as polyoxyethylene sorbitan monoesters (e.g. , Tween® 60) and polyoxy ethylene sorbitan polyesters (e.g., Tween® 20), ethers and polyethers such as polyethylene glycol monocetyl ether (cetomacrogol 1000) and polyethylene-polypropylene glycols (pluronics). In one embodiment, the water-miscible solvent includes PEG-400.

In some embodiments, the topical formulations for use as described herein also can include a penetration enhancer to improve delivery of the AMPK activator into the skin. Suitable penetration enhancers include, but are not limited to, alcohol, alkyl methyl sulfoxide, pyrrolidone, laurocapram, dimethyl formamide, tetrahydrofurfuryl alcohol, an amphiphile, or other miscellaneous enhancers such as clofibric acid amide, hexamethylene lauramide, dimethyl isosorbide, propylene glycol, proteolytic enzymes, terpenes or sesquiterpenes.

In some embodiments, the topical formulations for use as described herein also can include a surfactant. Suitable surfactants include, but are not limited to a sterol or sterol ester, for example cholesterol (cholesterin), lanolin (hydrous wool fat, lanum), anhydrous lanolin (wool fat, anhydrous lanum, agnin), or semi synthetic lanolin; carboxylic acids such as Na+, K+, ethanolamine salts of lauric acid, myristic acid, palmitic acid, stearic acid, oleic acid, or an ether or polyether such as polyethylene-polypropylene glycols (pluronics). If an oil-in-water (o/w) emulsifier is desired, the following examples may be used: esters and polyesters such as polyoxyethylene, sorbitan monoesters (Span™ 20, Span™ 40, Span™ 80), polyoxy ethylene esters (stearate-polyethylene glycol monoesters, Myrj® 45, Myrj® 59), polyoxy ethylene sorbitan polyesters (tweens); ethers and polyethers such as polyethylene glycol monocetyl ether (cetomacrogol 1000) or polyethylene-polypropylene glycols (pluronics), and others such as sodium lauryl sulfate, borax (sodium borate), ethanolamine, or triethanolamine. Nonionic surfactants, like Surfactant 190 (dimethicone copolyol), Polysorbate 20 (Tween® 20), Polysorbate 40 (Tween® 40), Polysorbate 60 (Tween® 60), Polysorbate 80 (Tween® 80), lauramide DEA, cocamide DEA, and cocamide MEA, amphoteric surfactants like oleyl betaine and cocamidopropyl betaine (Velvetex® BK-35), and cationic surfactants, like Phospholipid PTC (Cocamidopropyl phosphatidyl PG-dimonium chloride), can be used. Appropriate combinations or mixtures of such surfactants may also be used.

In some embodiments, the topical formulation comprises an antioxidant. Examples of anti-oxidants include, but are not limited to, butylated hydroxyanisole, butylated hydroxytoluene, ascorbic acid, a tocopherol, and combinations thereof, with particular embodiments comprising butylated hydroxytoluene as an antioxidant. In some embodiments, the topical formulations can include at least one emollient. Examples of suitable emollients include, but are not limited to, volatile and non-volatile silicone oils, highly branched hydrocarbons, and mixtures thereof.

In some embodiments, the topical formulation may further may include dyes/colorants and/or fragrances. Suitable fragrances and colors, such as 0.05% to 0.25% (w/w) caramel colorant caramel, FD&C Red No. 40 and FD&C Yellow No. 5, may be used in the formulations. Other examples of fragrances and colors suitable for use in topical products are known in the art.

The topical formulation comprising the AMPK activator optionally may comprise additional pharmaceutically acceptable ingredients such as additional solvents, gelling agents, fragrances, preservatives, anti-bacterial agents, diluents, stabilizers and/or adjuvants. However, such optional materials must not unduly interfere with the transdermal delivery of the drug active.

Examples of solvents include, but are not limited to, short chain alcohols and ethers; preferred optional solvent materials include polyethylene glycols, dipropylene glycol, ethylene glycol monoethyl ether, ethanol, isopropanol, and dimethyl isosorbide, or water may also be used as a solvent or co-solvent in the compositions of this invention.

Suitable fragrances and colors, such as caramel, FD&C Red No. 40 and FD&C Yellow No. 5, may be used in the formulations. Other examples of fragrances and colors suitable for use in topical products are known in the art.

In some embodiments, the topical formulation may also include other suitable additional and adjunct ingredients. Examples of such ingredients include, but are not limited to, absorbents (e.g., hydrogels), astringents (e.g., witch hazel, alcohol, and herbal extracts such as chamomile extract), binders (e.g., starch, cellulose ethers, microcrystalline cellulose, calcium hydrogen phosphate, calcium phosphate dibasic, and calcium sulfate dihydrate), other excipients (e.g., polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose), buffering agents (e.g., monobasic or dibasic potassium phosphate, monobasic or dibasic sodium phosphate, magnesium hydroxide), chelating agents (e.g., EDTA (ethylenediaminetetraacetic acid, tetrasodium salt)), film-forming agents (e.g., chitosan, hydroxypropylmethylcellulose, polyvinyl alcohol), conditioning agents (e.g., petrolatum, glycerin, propylene glycol), opacifying agents (e.g., titanium dioxide), pH adjusters (e.g., citric acid and sodium hydroxide), and protectants.

While particular embodiments of the present invention have been described, it will be obvious to those skilled in the art that various changes and modifications to the compositions disclosed herein can be made without departing from the spirit and the scope of the invention. It is intended to cover, in the appended claims, all such modifications that are within the scope of this invention.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLE 1

Materials and Methods

Experimental animals: Male ICR mice (Harlan, 20-25 g) were used for the study. All animal procedures were approved by the Institutional Animal Care and Use Committee of The University of Arizona and were in accordance with International Association for the Study of Pain guidelines.

Behavior testing: For the testing, animals were placed in acrylic boxes with wire mesh floors and allowed to habituate for approximately 1 h on all testing days. Paw withdrawal thresholds were measured using calibrated von Frey filaments (Stoelting, Wood Dale, Ill.) by stimulating the plantar aspect of left hind paw using the up-down method (Chaplan et al., 1994).

Plantar incision and behavioral testing: Prior to surgery all animals were assessed for paw withdrawal thresholds. A mouse model of incisional pain was used for this study (Banik et al., 2006). A 5 mm longitudinal incision was made with a number 11 blade through skin, fascia and muscle of the plantar aspect of the hind paw in isoflurane-anesthetized rats. Sham controls underwent the same procedure but without the incision. The skin was apposed with 2 sutures of 5 mm silk. Animals received intraplantar injection of resveratrol or vehicle around the incision at times indicated after incision. Animals were allowed to recover for 24 hrs and then paw withdrawal thresholds were measured at 24 hrs, 48 hrs, 5, 9, and 13 days post-surgery. For persistent sensitization experiments, the animals received an intraplantar injection of PGE2 (100 ng/25 µl) 14 days following incision or sham procedures. The paw withdrawal thresholds were again measured at 1 h, 3 h and 24 h following the PGE2 injection.

Immunohistochemistry: To determine re-epithelialization, plantar skin was excised from the left hind paw of mice either 3 days or 7 days following plantar incision surgery. The skin was immediately cryoprotected and frozen in O.C.T compound and sectioned (20 µm) on cryostat. The sections were then fixed in formalin and immersed in 0.1% hematoxylin for 3 minutes, washed in tap water, then immersed in 0.1% eosin for 3 minutes, and dehydrated through graded ethanol (Protocol from University of Michigan Center for Organogenesis). Finally sections were coverslipped with Permount (Fisher, Pittsburgh, Pa.). The sections were imaged and the width between 2 epithelial edges was measured using Olympus BX51 microscope.

Drugs and primary antibodies: Resveratrol was from Cayman Chemical; metformin from LKT laboratories. For the cream preparation with resveratrol, lyophilized resveratrol was serially dissolved in polyethylene glycol 400 (PEG 400) and solid PEG ointment to achieve a final concentration of 2 mg/ml. Hematoxylin Gill 2x, O.C.T. compound, Permount mounting medium and xylene were purchased from Fischer Scientific. Compound OSU 53 was synthesized by semi-manual solid-phase peptide synthesis (Boitano et al., 2011; Flynn et al., 2011; Josan et al., 2008; Lee et al., 2011; Vagner et al., 2008) performed in fritted syringes using a Domino manual synthesizer obtained from Torviq (Niles, Mich.). Crude peptides were purified by HPLC and size exclusion chromatography. Purity of the peptides was ensured using analytical HPLC (Waters Alliance 2695 separation model with a dual wavelength detector, Waters 2487) with a reverse-phase column (Waters Symmetry, 4.6×75 mm, 3.5 µm; flow rate, 0.3 ml/min). Structures were characterized by electrospray ionization on a Thermoelectron (Finnigan) LCQ ion trap instrument (low resolution), a Bruker Ultraflex III MALDI-TOF/TOF (low resolution), or a Bruker 9.4 T Fourier transform ion-cyclotron resonance (high resolution accurate mass) mass spectrometer.

Statistical Analysis and Data Presentation: Data are shown as means and the standard error of the mean (±SEM) of 6 animals (for behavioral studies). Graph plotting and statistical analysis used Graphpad Prism Version 5.03 (Graph Pad Software, Inc. San Diego, Calif., USA). Statistical evaluation was performed by one- or two-way analysis of variance (ANOVA), followed by appropriate post-hoc tests. The a priori level of significance at 95% confidence level was considered at $p<0.05$.

Results

Figure 1:
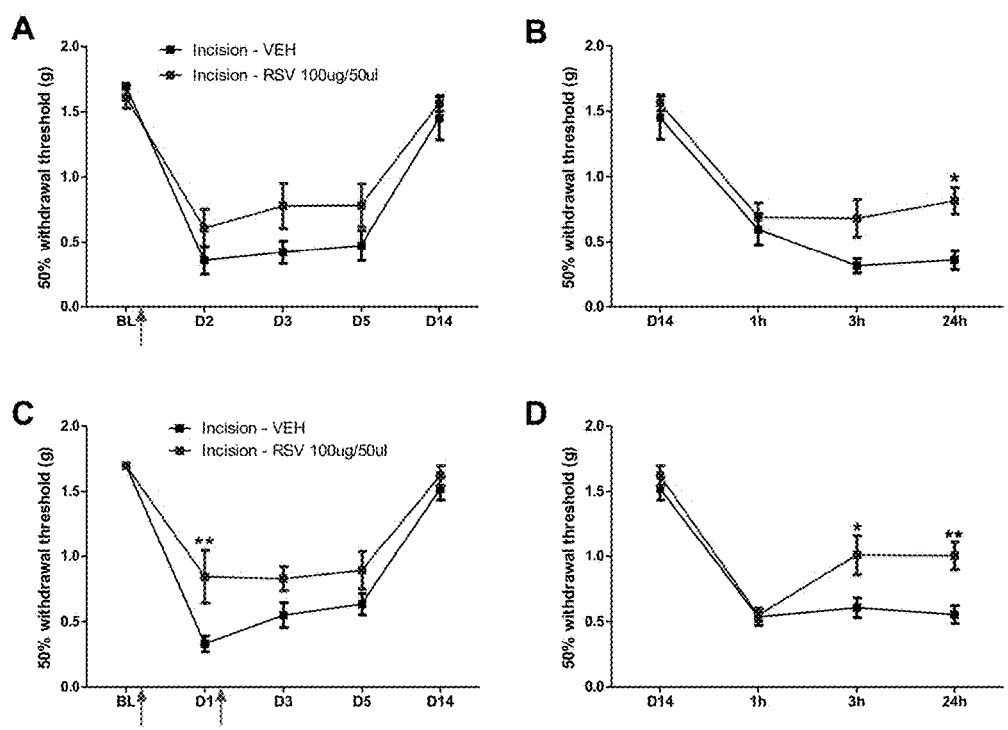
FIG. 1 shows that topical application of resveratrol inhibits acute mechanical hypersensitivity and hyperalgesic priming induced by plantar incision. Animals received a plantar incision on the left hind paw. Resveratrol (100 µg) or vehicle was applied on the paw on and around the incision either once, immediately following incision (A, B) or twice, immediately following incision as well as 24 hrs following incision (C, D). Mice were maintained under anesthesia with isoflurane for 1 hr until the drug was absorbed. A) Topical resveratrol (100 µg) application immediately following incision resulted in blunted incision-induced acute hypersensitivity B) Topical application of resveratrol (100 µg) immediately following incision abolished plantar incision-induced hyperalgesic priming precipitated by $PGE_2$ injection on day 14 after incision. C) Topical resveratrol (100 µg) application immediately following incision and at 1 day post incision significantly blocked plantar incision-induced acute hypersensitivity D) Topical application of resveratrol (100 µg) at the time of incision and at 1 day post incision significantly blocked plantar incision-induced hyperalgesic priming precipitated by $PGE_2$ injection on day 14 after incision.

Topical Resveratrol inhibits acute mechanical hypersensitivity and hyperalgesic priming induced by plantar incision: The present inventors have previously demonstrated that local injection of resveratrol, a potent AMPK activator, into the hind paw following plantar incision dose-relatedly reverses incision-mediated mechanical hypersensitivity as well as hyperalgesic priming induced by incision. Though resveratrol injection efficaciously blocked incision-induced allodynia, for clinical translability there is a need of better route of administration which is convenient and causes minimal discomfort. To address this issue, the present inventors made a novel cream preparation with resveratrol which can be applied topically. Lyophilized resveratrol was serially dissolved in polyethylene glycol 400 (PEG 400) and solid PEG ointment to achieve a final concentration of 2 mg/ml. A mouse model was utilized for incisional pain to assess if topical application of resveratrol can prevent development of allodynia following the plantar incision (Brennan et al., 1996; Pogatzki and Raja, 2003). Animals received a plantar incision on the left hindpaw. Resveratrol (100 µg) or vehicle was applied on the paw on and around the incision either immediately following incision or immediately following incision and 24 hrs following incision. Mice were maintained under anesthesia with isoflurane for 1 hr until the drug was absorbed. Mice with plantar incision that received vehicle displayed mechanical hypersensitivity lasting for at least 9 days. In contrast, animals that received topical resveratrol at the time of incision displayed blunted hypersensitivity though not significant (FIG. 1A). However, applying resveratrol topically twice i.e. at the time of incision and 24 hrs following incision, significantly attenuated mechanical hypersensitivity induced by incision (FIG. 1C). In this model, hyperalgesic priming can be revealed by a second intraplantar injection of inflammatory mediator $PGE_2$(100 ng) in the hind-paw, after the resolution of initial allodynia (Asiedu et al., 2011) following plantar incision. Topical application of resveratrol at the time of incision or at the time of incision and 1 day later both prevented the development of hyperalgesic priming precipitated by hind paw injection of $PGE_2$ following resolution of incision-induced mechanical hypersensitivity (FIGS. 1B and 1D). Thus, resveratrol not only blocks acute allodynia induced by plantar incision but it also blocks its transition to persistent nociceptive state. These results suggest that even local application of resveratrol can be a potentially efficacious treatment for post-surgical pain.

Figure 2:
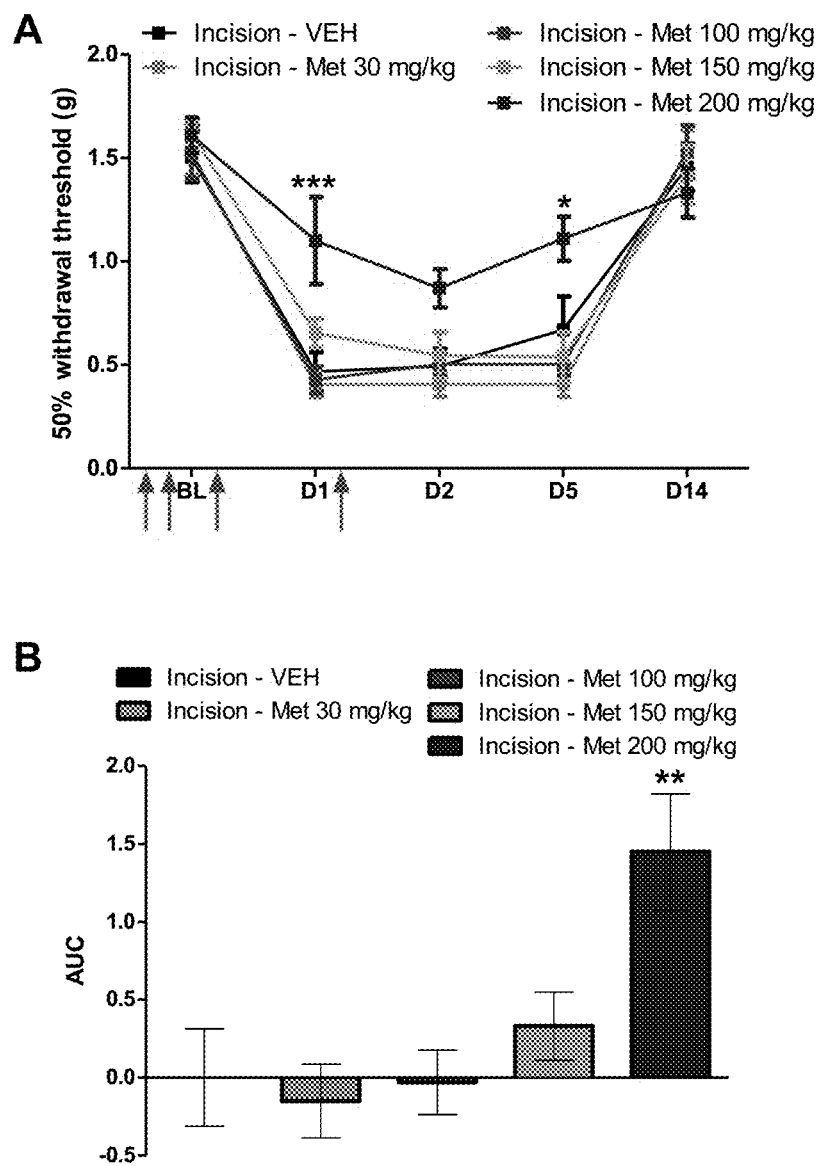
FIG. 2 shows metformin inhibits acute mechanical hypersensitivity induced by plantar incision. Animals received a plantar incision on the left hind paw. Metformin (30, 100, 150 or 200 mg/kg) or vehicle was injected intra-peritonially for 4 days starting 2 days prior to the surgery. A) Metformin (30, 100, 150 or 200 mg/kg) injection significantly blocked plantar incision-induced acute hypersensitivity. B) Area under the curve (AUC) analysis showing dose-related effects in A.
Figure 3:
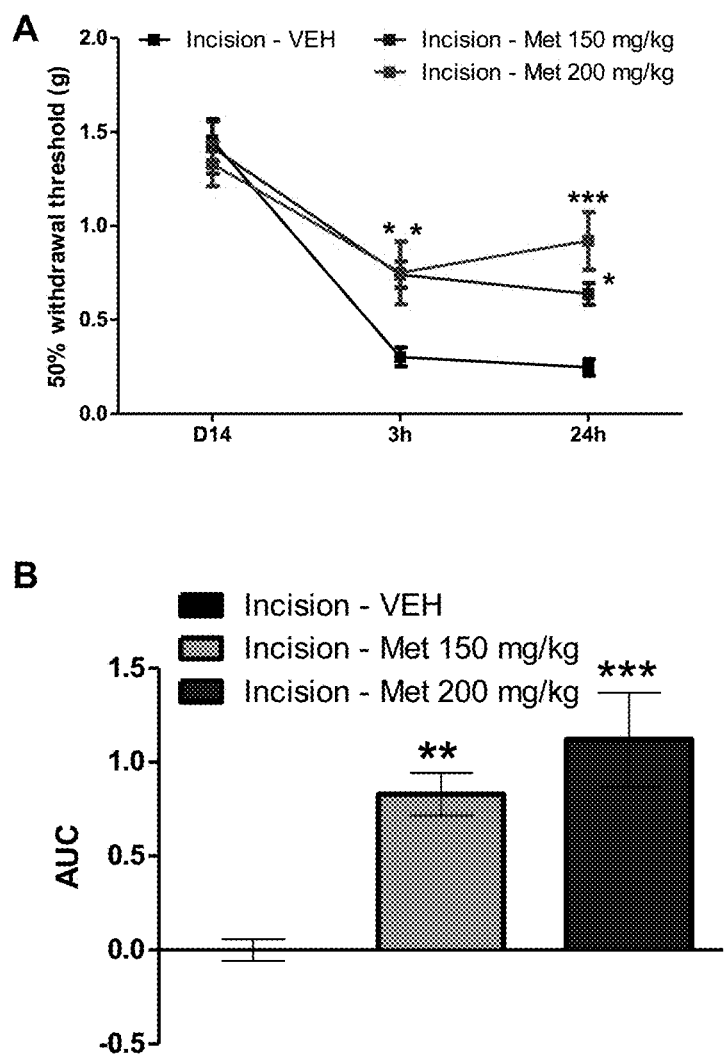
FIG. 3 shows metformin inhibits plantar incision-induced hyperalgesic priming precipitated by $PGE_2$ injection. Animals received a plantar incision on the left hind paw. Metformin (30, 100, 150 or 200 mg/kg) or vehicle was injected intraperitonially for 4 days starting 2 days prior to the surgery. Hyperalgesic priming was precipitated by a second intraplantar injection of inflammatory mediator $PGE_2$ (100 ng) in the hind paw on day 14 after incision. A) Metformin (30, 100, 150 or 200 mg/kg) injection significantly blocked plantar incision-induced hyperalgesic priming precipitated by $PGE_2$ injection on day 14 after incision. B) Area under the curve (AUC) analysis showing dose-related effects in A.

Metformin inhibits acute mechanical hypersensitivity and hyperalgesic priming induced by plantar incision: Another therapeutic opportunity for activating AMPK is the prototypical AMPK activator, metformin. Metformin is already clinically available, safe, inexpensive and well-tolerated drug. Moreover, metformin has a different mechanism of action in activating AMPK than resveratrol and hence can have differential efficacy in modulation of downstream targets. Metformin is known to activate AMPK through multiple indirect mechanisms including LKB1 stimulation (Shaw et al., 2005) and inhibition of AMP deaminase (Ouyang et al., 2011). In addition, in contrast to resveratrol which lacks bioavailability, metformin has a good bioavailability and thus can be given orally which is a preferred route of administration in humans. Hence, the present inventors investigated if systemic application of metformin can prevent development of incision-induced mechanical hypersensitivity and further hyperalgesic priming following the plantar incision. Animals received a plantar incision on the left hindpaw. Metformin (30, 100, 150 or 200 µg) or vehicle was injected intra-peritonially for 4 days starting 2 days prior to the surgery. Mice with plantar incision that received vehicle displayed long-lasting acute mechanical hypersensitivity (9 days) as well as hyperalgesic priming following $PGE_2$ lasting at least 24 hrs. In contrast, intra-peritonial injection of maximal dose (200 mg/kg) of metformin prevented both plantar-incision induced mechanical hypersensitivity (FIGS. 2A and 2B) and the expression of hyperalgesic priming following $PGE_2$ injection on day 14 (FIGS. 3A and 3B). Interestingly, the lower doses were not effective in blocking incision-induced acute mechanical hypersensitivity; however they significantly blocked hyperalgesic priming.

Figure 4:
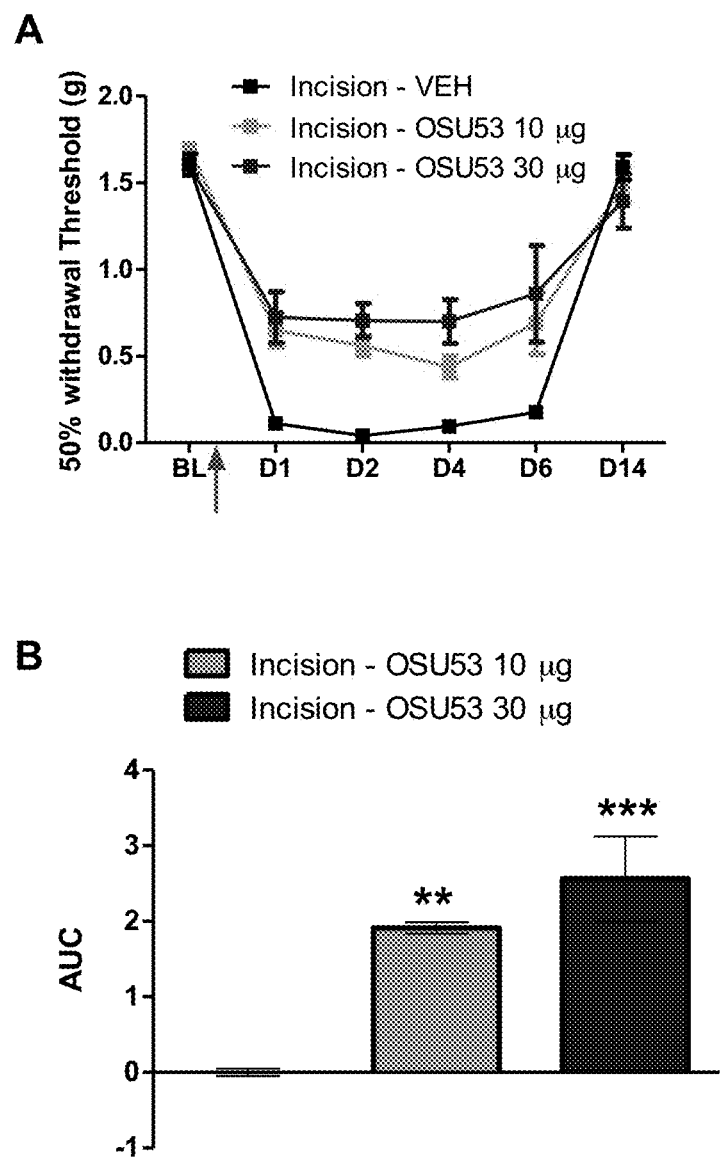
FIG. 4 shows OSU-53 inhibits acute mechanical hypersensitivity induced by plantar incision. Animals received a plantar incision on the left hind paw. OSU53 (10 or 30 µg) or vehicle was injected locally into the left hind paw around the incision immediately following incision and 24 hrs post-surgery. A) OSU53 (10 or 30 µg) injection significantly blocked plantar incision-induced acute hypersensitivity. B) Area under the curve (AUC) analysis showing dose-related effects in A.
Figure 5:
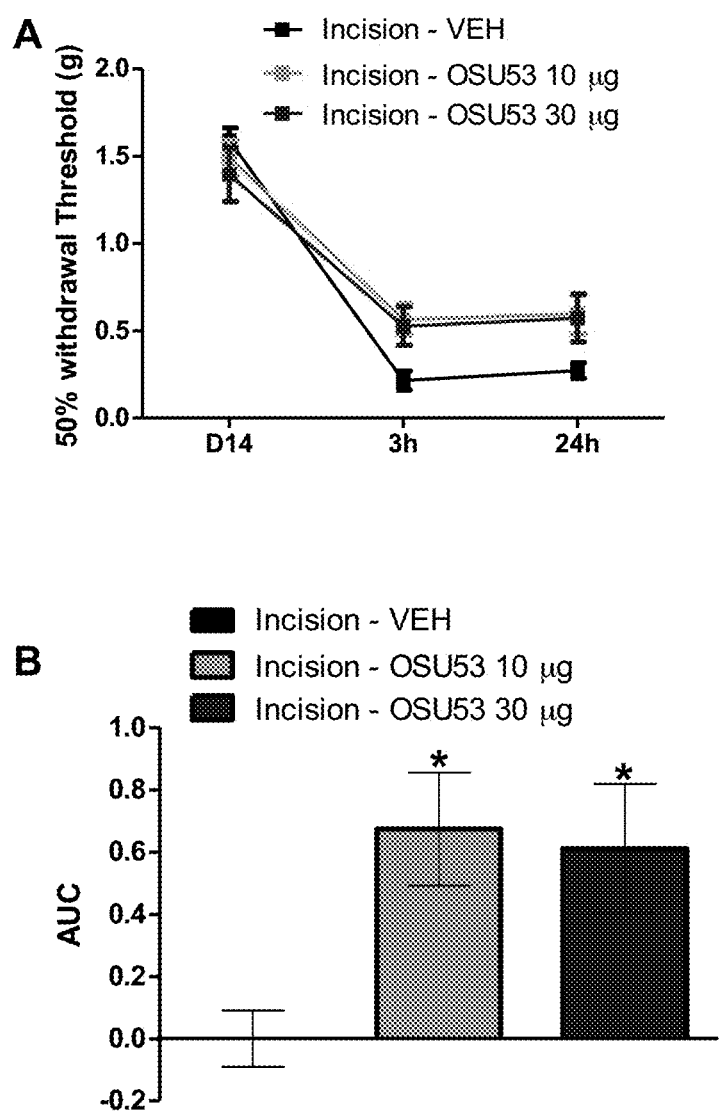
FIG. 5 shows OSU-53 inhibits plantar incision-induced hyperalgesic priming precipitated by $PGE_2$ injection. Animals received a plantar incision on the left hind paw. OSU53 (10 or 30 µg) or vehicle was injected locally into the left hind paw around the incision immediately following incision and 24 hrs post-surgery. Hyperalgesic priming was precipitated by a second intraplantar injection of inflammatory mediator $PGE_2$ (100 ng) in the hind paw on day 14 after incision. A) OSU53 (10 or 30 µg) injection significantly blocked plantar incision-induced hyperalgesic priming precipitated by $PGE_2$ injection on day 14 after incision. B) Area under the curve (AUC) analysis showing dose-related effects in A.

OSU53 inhibits acute mechanical hypersensitivity and hyperalgesic priming in a model of post-surgical pain in a dose-related manner. Although metformin is a clinically available and safe drug, the exact mechanism of action of metformin in activating AMPK is still unknown. Moreover, the effects of metformin have been attributed to AMPK-independent mechanisms as well (Foretz et al., 2010). Recently, a novel AMPK activator with a distinct mechanism of action, OSU53, was synthesized by scientists at Ohio State University (Lee et al., 2011). OSU53 stimulates AMPK kinase activity through direct activation with high potency ($EC_{50}$, 0.3 µM ) independent of its upstream kinase LKB1 (Lee et al., 2011), a mechanism distinct from that of metformin (Fryer et al., 2002; Lee et al., 2011; Shaw et al., 2005). Moreover, OSU53 is a potent, orally bioavailable AMPK activator making it a potential drug for treatment of post-surgical pain. The present inventors assessed if OSU53 prevented the development of acute hypersensitivity and hyperalgesic priming following plantar incision. Animals received a plantar incision on the left hindpaw. OSU53 (10 or 30 µg) or vehicle was injected locally into the left hind-paw around the incision either immediately following incision. Mice with plantar incision that received vehicle displayed long-lasting acute mechanical hypersensitivity as well as hyperalgesic priming following $PGE_2$ lasting at least 24 hrs. In contrast, intra-plantar injection of OSU53 dose-relatedly blocked both plantar-incision induced initial mechanical hypersensitivity (FIGS. 4A and 4B) and the expression of hyperalgesic priming after $PGE_2$ injection on day 14 (FIGS. 5A and 5B).

Figure 6:
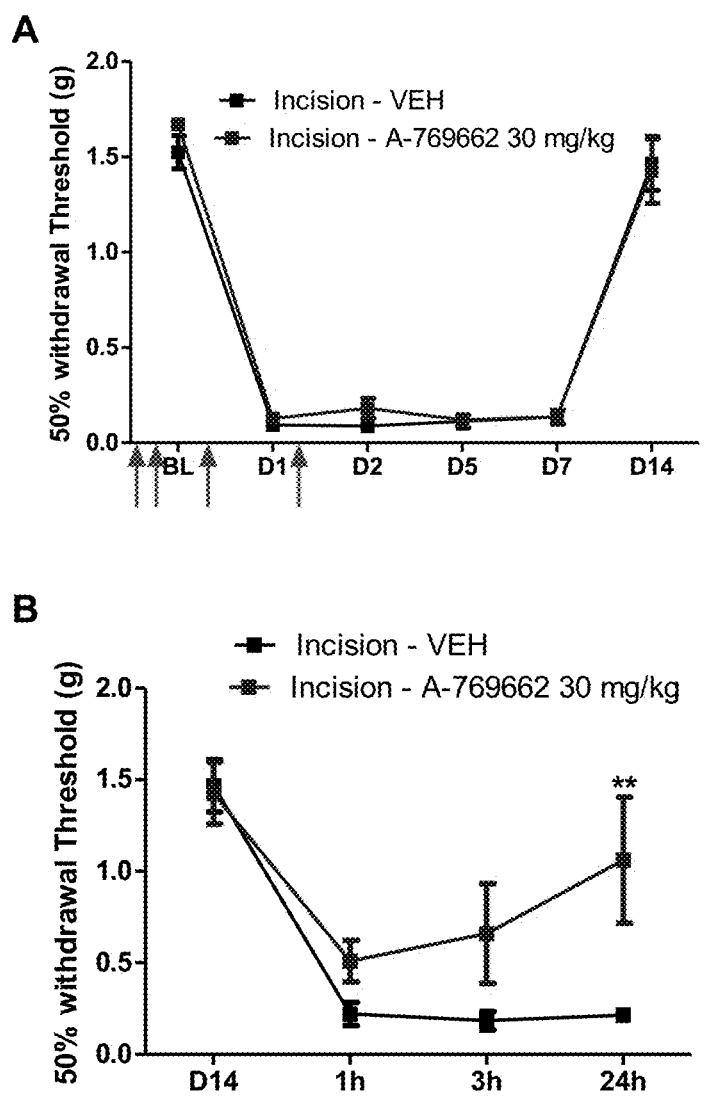
FIG. 6 shows A-769662 does not significantly inhibit acute mechanical hypersensitivity induced by plantar incision but blocks the hyperalgesic precipitated by $PGE_2$ injection. Animals received a plantar incision on the left hind paw. A-769662 (30 mg/kg) or vehicle was injected intra-peritonially for 4 days starting 2 days prior to the surgery. A) A-769662 (30 mg/kg) injection did not block plantar incision-induced acute hypersensitivity. B) A-769662 (30 mg/kg) injection significantly blocked plantar incision-induced hyperalgesic priming precipitated by $PGE_2$ injection on day 14 after incision.

A769662 doesn't inhibit acute mechanical hypersensitivity and but inhibits hyperalgesic priming in a model of post-surgical pain: Another direct activator of AMPK kinase is an investigational compound, A-769662. A-769662 activates AMPK both allosterically and inhibiting dephosphorylation of AMPK on Thr-172 (Sanders et al., 2007) and this activation is independent of upstream kinases (Goransson et al., 2007). The present inventors investigated if A-769662 prevented the development of acute hypersensitivity and hyperalgesic priming following plantar incision. Animals received a plantar incision on the left hindpaw. A-769662 (30 mg/kg) or vehicle was injected intra-peritonially for 4 days starting 2 days prior to the surgery. Mice with plantar incision that received vehicle displayed long-lasting acute mechanical hypersensitivity as well as hyperalgesic priming following $PGE_2$ lasting at least 24 hrs (FIGS. 6A and 6B). Interestingly, systemic A-769662 was not effective in blocking incision-induced acute mechanical hypersensitivity (FIG. 6A); however it significantly blocked hyperalgesic priming following $PGE_2$ injection (FIG. 6B).

Figure 7:
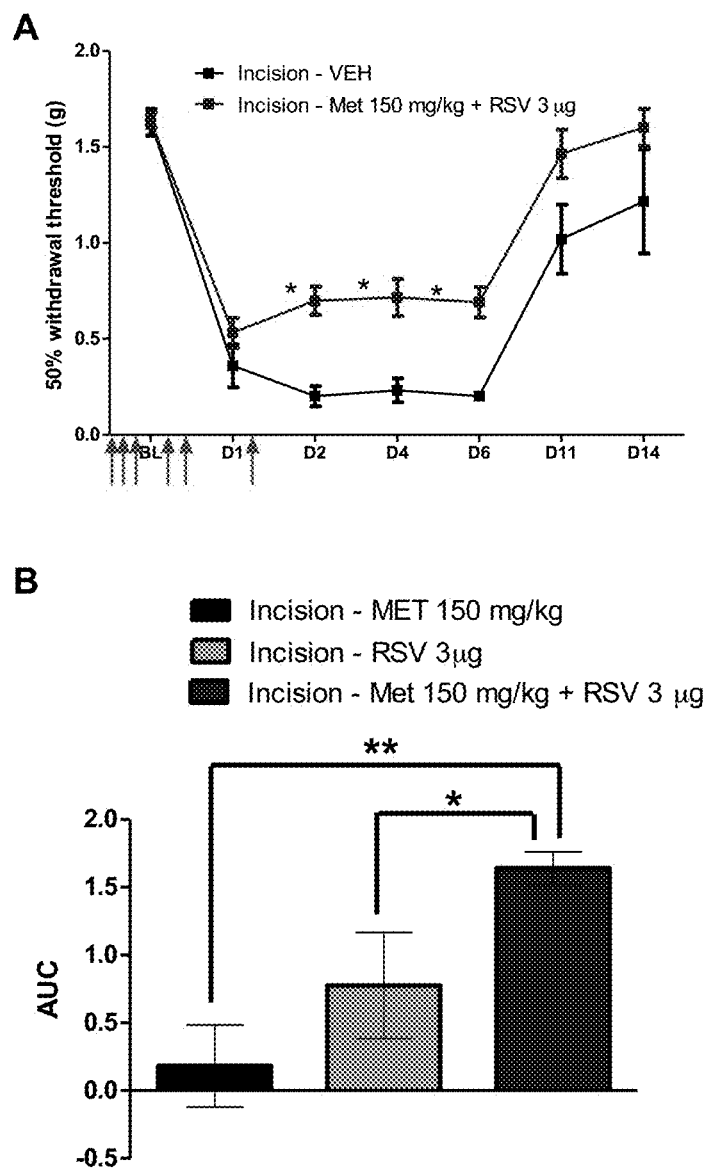
FIG. 7 shows co-treatment with systemic metformin and local resveratrol inhibits acute mechanical hypersensitivity induced by plantar incision. Animals received a plantar incision on the left hind paw. Metformin (150 µg) was injected intra-peritonially for 4 days starting 2 days prior to the surgery and resveratrol (3 µg) was injected in the left hind paw around the incision on the day of the surgery and 24 hrs post-surgery. A) Co-treatment with systemic metformin and local resveratrol significantly blocked plantar incision-induced acute hypersensitivity. B) Area under the curve (AUC) analysis showing dose-related effects in A compared to systemic metformin (150 μg) or local resveratrol (3 μg) alone.
Figure 8:
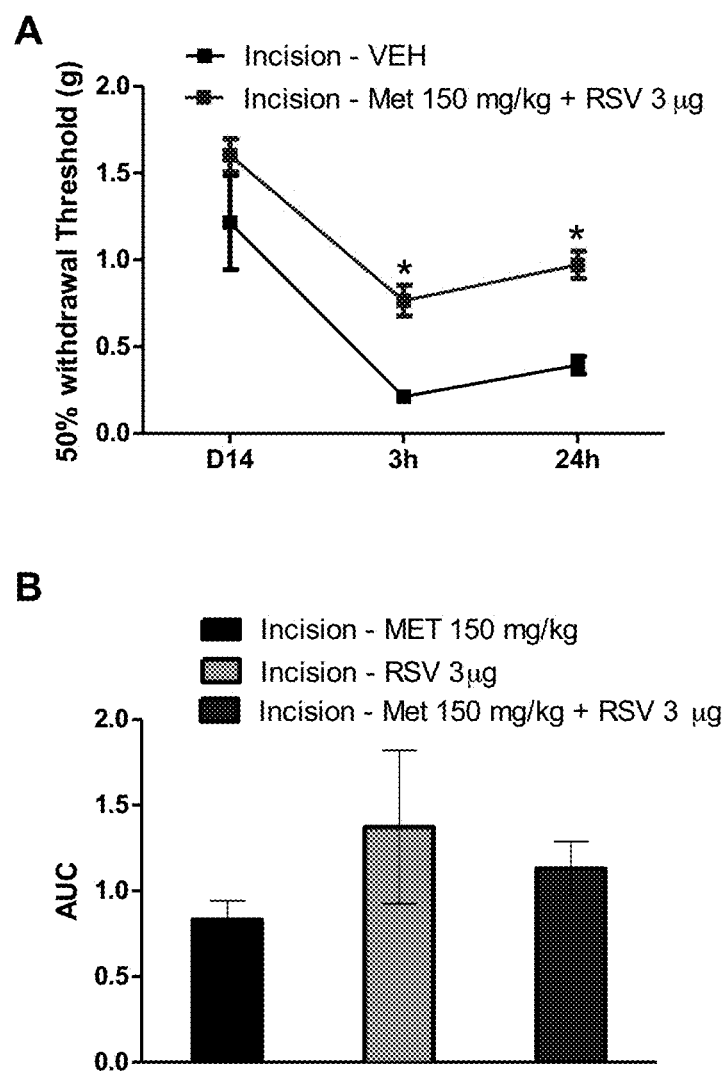
FIG. 8 shows co-treatment with systemic metformin and local resveratrol inhibits plantar incision-induced hyperalgesic precipitated by $PGE_2$ injection. Animals received a plantar incision on the left hind paw. Metformin (150 μg) was injected intra-peritonially for 4 days starting 2 days prior to the surgery and resveratrol (3 μg) was injected in the left hind paw around the incision on the day of the surgery and 24 hrs post-surgery. A) Co-treatment with systemic metformin and local resveratrol significantly blocked plantar incision-induced hyperalgesic priming precipitated by $PGE_2$ injection on day 14 after incision. B) Area under the curve (AUC) analysis showing dose-related effects in A compared to systemic metformin (150 μg) or local resveratrol (3 μg) alone.

Co-treatment with systemic metformin and local resveratrol inhibits acute mechanical hypersensitivity and hyperalgesic priming in a model of post-surgical pain: Although, all the AMPK activators individually entirely attenuate the development of the incision-induced hypersensitivity and hyperalgesic priming at the respective maximal doses, an effective treatment strategy would be to utilize sub-efficacious doses of AMPK activators and investigate if the co-treatment is equally efficacious in attenuating acute hypersensitivity and hyperalgesic priming following plantar incision. This strategy minimizes the unwanted side-effects of the drugs which occur while utilizing the maximal doses. Hence, the present inventors investigated if co-treatment of sub-efficacious dose of metformin and resveratrol can have added effect in attenuation of incision-induced mechanical hypersensitivity and hyperalgesic priming compared to their individual effects. Animals received a plantar incision on the left hind-paw and received treatment of vehicle, resveratrol or metformin alone or a co-treatment of metformin and resveratrol. Metformin (150 µg) was injected intra-peritonially for 4 days starting 2 days prior to the surgery and resveratrol (3 µg) was injected in the left hind-paw around the incision on the day of the surgery and 24 hrs post-surgery. Mice with plantar incision that received vehicle displayed long-lasting acute mechanical hypersensitivity as well as hyperalgesic priming following $PGE_2$. Mice which received metformin or resveratrol alone displayed blunted acute hypersensitivity compared to vehicle treated mice but the effect was not significant (FIG. 7A). In contrast, co-treatment with systemic metformin and local resveratrol at individually sub-efficacious doses at the time of incision significantly attenuated acute hypersensitivity (FIGS. 7A and 7B) and hyperalgesic priming (FIGS. 8A and 8B) suggesting potential super-additive effects of combined AMPK activator use.

Figure 9:
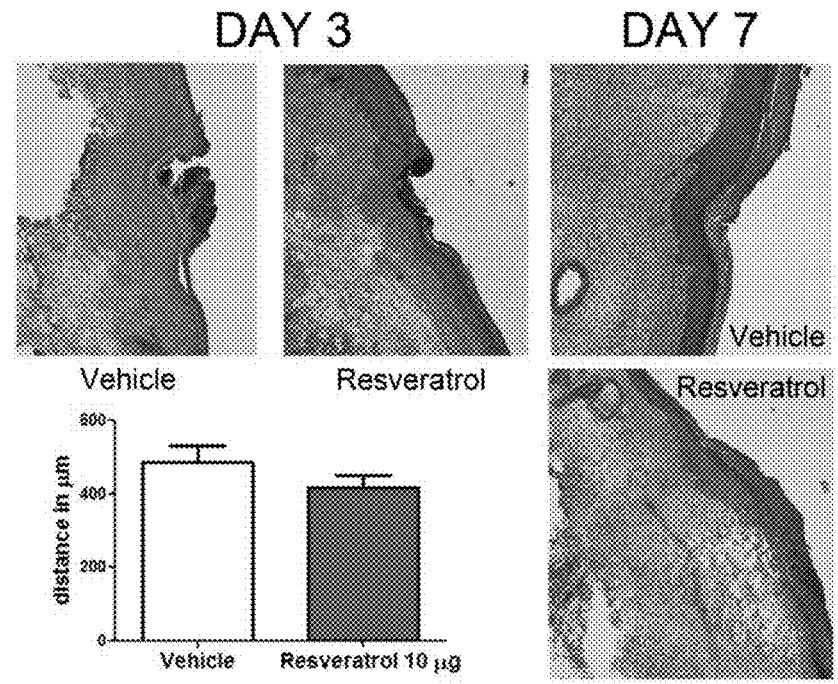
FIG. 9 shows AMPK activators don't appear to affect wound healing negatively in a model of post-surgical pain. Animals received a plantar incision on the left hind paw. Skin from the left hind paw was excised 3 and 7 days after plantar incision and wound healing and wound closure was assessed using Hematoxylin & Eosin (H & E) staining. A) Resveratrol (10 μg) or vehicle was injected in the left hind paw around the incision on the day of the surgery and 24 hrs post-surgery. There was no difference in the wound size between the resveratrol and vehicle treated groups on Day 3. The wound was completely closed by Day 7 in the animals in both groups receiving vehicle or resveratrol. B) Metformin (200 mg/kg) or vehicle was injected intra-peritonially for 4 days starting 2 days prior to the surgery. No differences were noted in the wound size between the metformin and vehicle treated groups on Day 3. The wound was completely closed by Day 7 in the animals in both groups receiving vehicle or metformin. C) OSU53 (10 or 30 μg) or vehicle was injected locally into the left hind paw around the incision immediately following incision and 24 hrs post-surgery. There was no diiference in the wound size between the OSU53 and vehicle treated groups on Day 3. The wound was completely closed by Day 7 in the animals in both groups receiving vehicle or OSU53.
Figure 9:
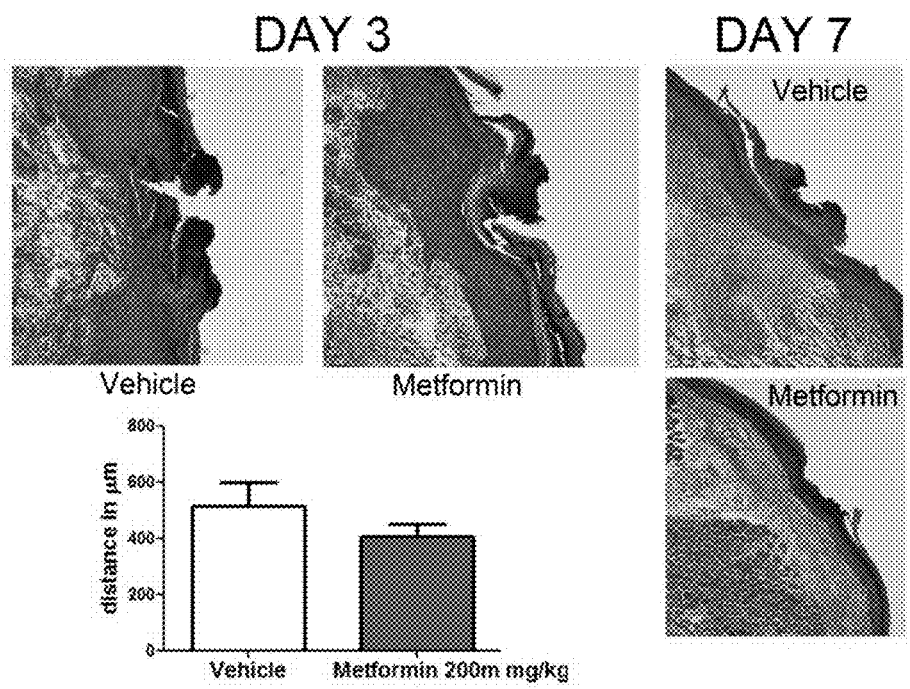
Figure 9:
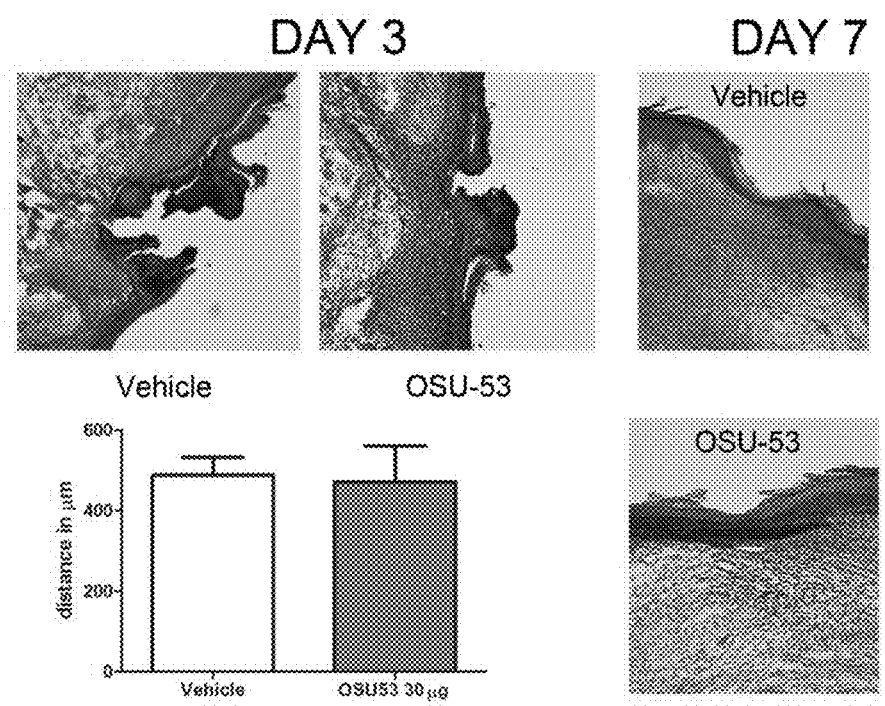

AMPK activators don't affect wound healing negatively in a model of post-surgical pain: An important potential consideration in these experiments is that AMPK activators would be expected to reduce protein translation and therefore may negatively influence wound healing. This effect would have a negative impact on their clinical utility. To test if AMPK activators affect the wound healing, we utilized either vehicle or maximal doses of the AMPK activators (resveratrol or metformin or OSU53) described in the previous experiments and assessed wound healing with Hematoxylin & Eosin (H & E) staining (Lai et al., 2009). Skin samples were excised 3 and 7 days after plantar incision to assess healing and wound closure, respectively. For the animals treated with resveratrol, no differences were noted in the wound size between the resveratrol and vehicle treated groups on Day 3 (FIG. 9A). By Day 7, the wound was completely closed in the animals in both groups receiving vehicle or resveratrol (FIG. 9A). Similar results were obtained with intra-peritonial metformin or intra-plantar OSU53 treatment (FIGS. 9B and 9C). Thus, a lack of effect on with AMPK activators would suggest that these compounds would be unlikely to interfere with the wound healing process.

EXAMPLE 2

Case Study (1) Patient A, a 28 year old female, presents for a scheduled cesarean section. Vial signs and labs appear normal. Obstetrician makes a low transverse incision, and delivery proceeds normally. Approximately 18 hours after surgery, Patient A is administered a sub-efficacious dose of biguanide AMPK activator metformin and a sub-efficacious dose of AMPK activator A769662 to help prevent incision-induced pain such as chronic pain development. Follow up with Patient A regarding incision-induced pain occurs bi-weekly for six weeks post-op. Patient A experiences little incision-induced pain within 5 days post-op, and no pain is observed by 3 weeks post-op.

(2) Patient B, a 55 year-old male, present to surgery for gastric banding surgery. Before anesthesia is initiated, Patient B is administered a sub-efficacious dose of biguanide AMPK activator phenformin and a sub-efficacious dose of AMPK activator leptin to help prevent incision-induced pain such as chronic pain development. Surgeon makes several small incisions in the abdomen, and the banding procedure proceeds normally. Follow up with Patient B regarding incision-induced pain occurs weekly for eight weeks post-op. Patient B experiences minor incision-induced pain within 1 week post-op, and no pain is observed by 2 weeks post-op.

(3) Patient C, a 35 year-old female, present to orthopedic surgery for ACL repairs. Immediately following surgery, Patient C is administered locally both a sub-efficacious dose of AICAR and a sub-efficacious dose of AMPK activator berberine to help prevent incision-induced pain such as chronic pain development. Follow up with Patient C regarding incision-induced pain occurs daily for six weeks post-op. Patient C experiences no incision-induced pain within 2 weeks post-op.

(4) Patient D, an 85 year-old female, present to orthopedic surgery for hip replacement. Prior to surgery, Patient D is administered systemically a sub-efficacious dose of AMPK activator rosiglitazone and a sub-efficacious dose of AMPK activator OSU53 to help prevent incision-induced pain such as chronic pain development. Follow up with Patient D regarding incision-induced pain occurs daily for five weeks post-op. Patient D experiences minor incision-induced pain within 1 week post-op and experiences no incision-induced pain within 3 weeks post-op.

(5) Patient E, a 22 year-old male, present to trauma surgery for motor vehicle accident (MVA)-related trauma to the ribs and lungs. During surgery, Patient E is administered systemically both a sub-efficacious dose of AMPK activator IL-6 and a sub-efficacious dose of AMPK activator proguanil to help prevent trauma-and incision-induced pain such as chronic pain development. Follow up with Patient E regarding pain occurs daily for eight weeks post-op. Patient E experiences minor incision-induced pain up to 3 weeks post-op, but no incision-induced pain is observed within 4 weeks post-op.

(6) Patient F, a 65 year-old male, presents to the emergency department for chest pain. Initial tests indicate Patent F is experiencing a myocardial infarction (MI). Patient F is immediately taken to surgery for coronary artery bypass grafting. Twelve hours after surgery, Patient F is administered systemically both a sub-efficacious dose of AMPK activator ciliary neurotrophic factor (CNTF) and a sub-efficacious dose of AMPK activator salicylate to help prevent incision-induced pain such as chronic pain development. Follow up with Patient F regarding incision-induced pain occurs daily for four weeks post-op. Patient F experiences no incision-induced pain within 2 weeks post-op.

CITED REFERENCES

Asiedu, M. N., Tillu, D. V., Melemedjian, O. K., Shy, A., Sanoja, R., Bodell, B., Ghosh, S., Porreca, F., and Price, T. J. (2011). Spinal protein kinase M zeta underlies the maintenance mechanism of persistent nociceptive sensitization. The Journal of neuroscience: the official journal of the Society for Neuroscience 31, 6646-6653.

Banik, R. K., Subieta, A. R., Wu, C., and Brennan, T. J. (2005). Increased nerve growth factor after rat plantar incision contributes to guarding behavior and heat hyperalgesia. Pain 117, 68-76.

Banik, R. K., Woo, Y. C., Park, S. S., and Brennan, T. J. (2006). Strain and sex influence on pain sensitivity after plantar incision in the mouse. Anesthesiology 105, 1246-1253.

Boitano, S., Flynn, A. N., Schulz, S. M., Hoffman, J., Price, T. J., and Vagner, J. (2011). Potent agonists of the protease activated receptor 2 (PAR2). Journal of medicinal chemistry 54, 1308-1313.

Brennan, T. J., Vandermeulen, E. P., and Gebhart, G. F. (1996). Characterization of a rat model of incisional pain. Pain 64, 493-501.

Bryan, D., Walker, K. B., Ferguson, M., and Thorpe, R. (2005). Cytokine gene expression in a murine wound healing model. Cytokine 31, 429-438.

Chaplan, S. R., Bach, F. W., Pogrel, J. W., Chung, J. M., and Yaksh, T. L. (1994). Quantitative assessment of tactile allodynia in the rat paw. Journal of neuroscience methods 53, 55-63.

Crombie, I. K., Davies, H. T., and Macrae, W. A. (1998). Cut and thrust: antecedent surgery and trauma among patients attending a chronic pain clinic. Pain 76, 167-171.

Flynn, A. N., Tillu, D. V., Asiedu, M. N., Hoffman, J., Vagner, J., Price, T. J., and Boitano, S. (2011). The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. The Journal of biological chemistry 286, 19076-19088.

Foretz, M., Hebrard, S., Leclerc, J., Zarrinpashneh, E., Soty, M., Mithieux, G., Sakamoto, K., Andreelli, F., and Viollet, B. (2010). Metformin inhibits hepatic gluconeogenesis in mice independently of the LKB1/AMPK pathway via a decrease in hepatic energy state. The Journal of clinical investigation 120, 2355-2369.

Fryer, L. G., Parbu-Patel, A., and Carling, D. (2002). The Anti-diabetic drugs rosiglitazone and metformin stimulate AMP-activated protein kinase through distinct signaling pathways. The Journal of biological chemistry 277, 25226-25232.

Geranton, S. M., Jimenez-Diaz, L., Torsney, C., Tochiki, K. K., Stuart, S. A., Leith, J. L., Lumb, B. M., and Hunt, S. P. (2009). A rapamycin-sensitive signaling pathway is essential for the full expression of persistent pain states. The Journal of neuroscience: the official journal of the Society for Neuroscience 29, 15017-15027.

Goransson, O., McBride, A., Hawley, S. A., Ross, F.A., Shpiro, N., Foretz, M., Viollet, B., Hardie, D. G., and Sakamoto, K. (2007). Mechanism of action of A-769662, a valuable tool for activation of AMP-activated protein kinase. The Journal of biological chemistry 282, 32549-32560.

Huang, H. L., Cendan, C. M., Roza, C., Okuse, K., Cramer, R., Timms, J. F., and Wood, J. N. (2008). Proteomic profiling of neuromas reveals alterations in protein composition and local protein synthesis in hyper-excitable nerves. Molecular pain 4, 33.

Jimenez-Diaz, L., Geranton, S. M., Passmore, G. M., Leith, J. L., Fisher, A. S., Berliocchi, L., Sivasubramaniam, A. K., Sheasby, A., Lumb, B .M., and Hunt, S. P. (2008). Local translation in primary afferent fibers regulates nociception. PloS one 3, e1961.

Johansen, A., Romundstad, L., Nielsen, C. S., Schirmer, H., and Stubhaug, A. (2012). Persistent postsurgical pain in a general population: Prevalence and predictors in the Tromso study. Pain 153, 1390-1396.

Josan, J. S., Vagner, J., Handl, H.L., Sankaranarayanan, R., Gillies, R. J., and Hruby, V. J. (2008). Solid-Phase Synthesis of Heterobivalent Ligands Targeted to Melanocortin and Cholecystokinin Receptors. International journal of peptide research and therapeutics 14, 293-300.

Kehlet, H., Jensen, T .S., and Woolf, C. J. (2006). Persistent postsurgical pain: risk factors and prevention. Lancet 367, 1618-1625.

Lai, J. J., Lai, K .P., Chuang, K. H., Chang, P., Yu, I. C., Lin, W. J., and Chang, C. (2009). Monocyte/macrophage androgen receptor suppresses cutaneous wound healing in mice by enhancing local TNF-alpha expression. The Journal of Clinical Investigation 119, 3739-3751.

Lee, K. H., Hsu, E. C., Guh, J. H., Yang, H. C., Wang, D., Kulp, S. K., Shapiro, C. L., and Chen, C. S. (2011). Targeting energy metabolic and oncogenic signaling pathways in triple-negative breast cancer by a novel adenosine monophosphate-activated protein kinase (AMPK) activator. The Journal of biological chemistry 286, 39247-39258.

Matsuda, H., Koyama, H., Sato, H., Sawada, J., Itakura, A., Tanaka, A., Matsumoto, M., Konno, K., Ushio, H., and Matsuda, K. (1998). Role of nerve growth factor in cutaneous wound healing: accelerating effects in normal and healing-impaired diabetic mice. The Journal of experimental medicine 187, 297-306.

Melemedjian, O. K., Asiedu, M. N., Tillu, D. V., Peebles, K. A., Yan, J., Ertz, N., Dussor, G. O., and Price, T. J. (2010). IL-6-and NGF-induced rapid control of protein synthesis and nociceptive plasticity via convergent signaling to the eIF4F complex. The Journal of neuroscience: the official journal of the Society for Neuroscience 30, 15113-15123.

Ouyang, J., Parakhia, R. A., and Ochs, R. S. (2011). Metformin activates AMP kinase through inhibition of AMP deaminase. The Journal of biological chemistry 286, 1-11.

Pogatzki, E. M., and Raja, S. N. (2003). A mouse model of incisional pain. Anesthesiology 99, 1023-1027.

Sanders, M. J., Ali, Z. S., Hegarty, B. D., Heath, R., Snowden, M. A., and Carling, D. (2007). Defining the mechanism of activation of AMP-activated protein kinase by the small molecule A-769662, a member of the thienopyridone family. The Journal of biological chemistry 282, 32539-32548.

Sato, Y., and Ohshima, T. (2000). The expression of mRNA of proinflammatory cytokines during skin wound healing in mice: a preliminary study for forensic wound age estimation (II). International journal of legal medicine 113, 140-145.

Shaw, R. J., Lamia, K. A., Vasquez, D., Koo, S. H., Bardeesy, N., Depinho, R. A., Montminy, M., and Cantley, L. C. (2005). The kinase LKB1 mediates glucose homeostasis in liver and therapeutic effects of metformin. Science 310, 1642-1646.

Vagner, J., Xu, L., Handl, H. L., Josan, J. S., Morse, D. L., Mash, E. A., Gillies, R. J., and Hruby, V. J. (2008). Heterobivalent ligands crosslink multiple cell-surface receptors: the human melanocortin-4 and delta-opioid receptors. Angewandte Chemie 47, 1685-1688.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

The foregoing discussion of the invention has been presented for purposes of illustration and description. Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures.

It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed:

1. A method of reducing incision-induced hypersensitivity, incision-induced hyperalgesic priming, or incision-induced development of chronic pain in a subject, said method comprising topically administering to the subject a dosage of a first 5'-adenosine monophosphate-activated protein kinase (AMPK) activator and a dosage of a second AMPK activator, the first AMPK activator is metformin and the second AMPK activator is resveratrol, wherein the dosage of the first AMPK activator is an individually sub-efficacious dose, and the dosage of the second AMPK activator is an individually sub-efficacious dose, wherein the first AMPK activator and the second AMPK activator synergistically reduce incision-induced hypersensitivity, incision-induced hyperalgesic priming, or incision-induced development of chronic pain.

2. The method of claim 1, wherein the sub-efficacious dose of the first AMPK activator is a dose that is less than the first AMPK activator's threshold dose.

3. The method of claim 1, wherein the sub-efficacious dose of the second AMPK activator is a dose that is less than the second AMPK activator's threshold dose.

4. The method of claim 1, wherein the sub-efficacious dose of the first AMPK activator is a dose that is less than the first AMPK activator's $EC_{50}$.

5. The method of claim 1, wherein the sub-efficacious dose of the second AMPK activator is a dose that is less than the second AMPK activator's $EC_{50}$.

6. The method of claim 1, wherein the sub-efficacious dose of the first AMPK activator is a dose that is between the first AMPK activator's $EC_{50}$ and threshold dose.

7. The method of claim 1, wherein the sub-efficacious dose of the second AMPK activator is a dose that is between the second AMPK activator's $EC_{50}$ and threshold dose.

* * * * *